(12) United States Patent
Chen et al.

(10) Patent No.: US 7,235,631 B2
(45) Date of Patent: Jun. 26, 2007

(54) ICOS MUTANTS

(75) Inventors: Lieping Chen, Rochester, MN (US); Jürgen Bajorath, Lynnwood, WA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 483 days.

(21) Appl. No.: 10/072,622

(22) Filed: Feb. 7, 2002

(65) Prior Publication Data

US 2003/0158102 A1 Aug. 21, 2003

(51) Int. Cl.
C07K 14/47 (2006.01)
C07K 14/725 (2006.01)
C07K 16/46 (2006.01)

(52) U.S. Cl. .................................. 530/350; 530/387.3

(58) Field of Classification Search ................. 530/350; 514/12, 21
See application file for complete search history.

(56) References Cited

U.S. PATENT DOCUMENTS 6,521,749 B1 * 2/2003 Ling et al. ................. 536/23.5
6,630,575 B2 * 10/2003 Coyle et al. ................. 530/350
2002/0156242 A1 * 10/2002 Tamatani et al. ........... 530/350

OTHER PUBLICATIONS

Wang et al., J. Exp. Med., 2002, 8: 1033-1041.*
Attwood, Science 2000; 290:471-473.*
Skolnick et al., Trends in Biotech. 2000; 18(1):34-39.*
Metzler et al., Nature Structural Biol. 1997; 4:527-531.*
Bajorath et al., "Molecular modeling of CD28 and three-dimensional analysis of residue conservation in the CD28/CD152 family," *Journal of Molecular Graphics and Modelling*, 1997, 15(2):135-139.
Bajorath, "A Molecular Model of Inducible Costimulator Protein and Three-Dimensional Analysis of its Relation to the CD28 Family of T Cell-Specific Costimulatory Receptors," *J. Mol. Model.*, 1999, 5:169-176.
Boise et al., "CD28 and apoptosis," *Curr. Opin. Immunol.*, 1995, 7:620-625.
Buonfiglio et al., "The T cell activation molecule H4 and the CD28-like molecule ICOS are identical," *Eur. J. Immunol.*, 2000, 30:3463-3467.
Chambers and Allison, "Co-stimulation in T cell responses," *Curr. Opin. Immunol.*, 1997, 9:396-404.
Dong et al., "B7-H1, a third member of the B7 family, co-stimulates T-cell proliferation and interleukin-10 secretion," *Nature Medicine*, 1999, 5(12):1365-1369.
Hunkapiller and Hood, "Diversity of the Immunoglobulin Gene Superfamily," *Adv. Immunol.*, 1989, 44:1-63.
Hutloff et al., "ICOS is an inducible T-cell co-stimulator structurally and functionally related to CD28," *Nature*, 1999, 397:263-266.
Krummel and Allison, "CTLA-4 Engagement Inhibits IL-2 Accumulation and Cell Cycle Progression upon Activation of Resting T Cells," *J. Exp. Med.*, 1996, 183:2533-2540.
Lenschow et al., "CD28/B7 System of T Cell Costimulation," *Annu. Rev. Immunol.*, 1996, 14:233-258.
Linsley and Ledbetter, "The Role of the CD28 Receptor During T Cell Responses to Antigen," *Annu. Rev. Immunol.*, 1993, 11:191-212.
Lucia et al., "Expression of the Novel T Cell Activation Molecule hpH4 in HIV-Infected Patients: Correlation with Disease Status," *Aids Research and Human Retroviruses*, 2000, 16(6):549-557.
Metzler et al., "Solution structure of human CTLA-4 and delineation of a CD80/CD86 binding site conserved in CD28," *Nature Structural Biology*, 1997, 4(7):527-531.
Peach et al., "Complementarity Determining Region 1 (CDR1)- and CDR3-analogous Regions in CTLA-4 and CD28 Determine the Binding to B7-1," *J. Exp. Med.*, 1994, 180:2049-2058.
Rathmell and Thompson, "The Central Effectors of Cell Death in the Immune System," *Annu. Rev. Immunol.*, 1999, 17:781-828.
Walunas et al., "CTLA-4 Ligation Blocks CD28-dependent T Cell Activation," *J. Exp. Med.*, 1996, 183:2541-2550.
Wang et al., "Costimulation of T cells by B7-H2, a B7-like molecule that binds ICOS," *Blood*, 2000, 96(8):2808-2813.
Yoshinaga et al., "T-cell co-stimulation through B7RP-1 and ICOS," *Nature*, 1999, 402:827-832.
Yoshinaga et al., "Characterization of a new human B7-related protein: B7RP-1 is the ligand to the co-stimulatory protein ICOS," *International Immunology*, 2000, 12(10):1439-1447.

* cited by examiner

*Primary Examiner*—Phillip Gambel
*Assistant Examiner*—Ilia Ouspenski
(74) *Attorney, Agent, or Firm*—Fish & Richardson P.C.

(57) ABSTRACT

Purified ICOS polypeptides are described, as well as nucleic acids encoding the polypeptides, vectors including the nucleic acids, host cells containing the vectors, and methods for using the polypeptides, nucleic acids, and host cells.

9 Claims, 7 Drawing Sheets

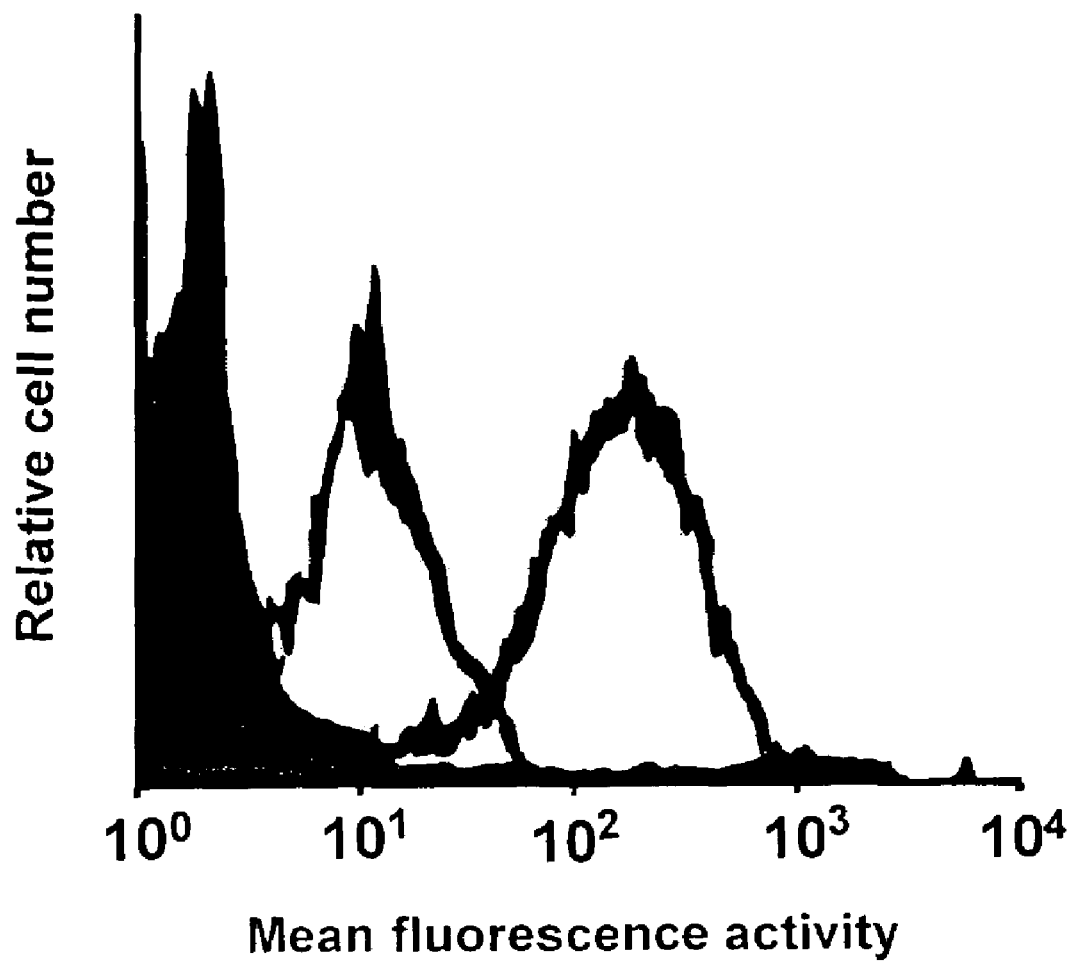

```
                                                  ! ! ! !                      !
              A      A'        B         *  *  C            *C'
mCTLA-4   vTq.pSVVLaSSHGVASfPCEYSPSHNTDEVRvTvLRQTNDQMTEvCAT
rCTLA-4   vTq.pSVVLaSSHGVASfPCEYASSHNTDEVRvTvLRQTNDQVTEvCAT
hCTLA-4   vAq.pAVVLaSSRGIASfVcEYASPGKATEVRvTvLRQADSQVTEvCAA
bCTLA-4   vSq.pAVVLaSSRGVASfVcEYASSHKATEVRvTvLRQANSQMTEvCAM
  mCD28   vKqSpLLVVdSN..EVSlScRYSYNLLAKEFRaSlYKGV.NSDVEvCVG
  rCD28   vKqSpLLVVdNN..EVSlScRYSYNLLAKEFRaSlYKGV.NSDVEvCVG
  bCD28   vKqSpMLVVnNN..EVNlScKYTYNLFSKEFRaSlYKGA.DSAVEvCVV
  hCD28   vKqSpMLVAyDN..AVNlScKYSYNLFSREFRaSlHKGL.DSAVEvCVV
  mICOS   aDhR.MFSFh.N.GGVQiScKYP.DIV.QQLKmRlFRE..REV..lCEL
  hICOS   aNyE.MFIFh.N.GGVQiLcKYP.DIV.QQFKmQlLKG..GQI..lCDL
                 30        40        50        60

!  !         !
              C"         D         E               F     *
mCTLA-4   TFTEK..NTVGFLDYPfCSgTFNESRvNlTiQGlRAVDTGLyLcKvE
rCTLA-4   TFTVK..NTLGFLDDPfCSgTFNESRvNLTiQGlRAADTGLyFcKvE
hCLTA-4   TYMMG..NELTFLDDSICTgTSSGNQvNlTiQGlRAMDTGLyIcKvE
bCTLA-4   TYTVE..NELTFIDDStCTgISHGNKvNlTiQGlSAMDTGLyIcKvE
  mCD28   NGNFTYQPQFRSNAEFnCDgDFlNETvTfRlWNlHVNHTDIyFcKiE
  rCD28   NGNFTYQPQFRPNVGFnCDgNFlNETvTfRlWNlDVNHTDIyFcKiE
  bCD28   NGNFSHPHQFHSTTGFnCDgKLGNETvTfYlKNlYVNQTDIyFcKiE
  hCD28   YGNYSQQLQVYSKTGFnCDgKLGNESvTfYlQNlYVNQTDIyFcKiE
  mICOS   TKTKGSGNAVSIKNPMlCLyHLSNNSvSfFlNNpDSSQGSYyFcSlS
  hICOS   TKTKGSGNTVSIKSLKfCHsQLSNNSvSfFlYNlDHSHANYyFcNlS
                 70        80        90       100       110

!! ! !
          * * * * * *        G
mCTLA-4   LMYPPPYF.VGMGNGTQiYvIDPEPC
rCTLA-4   LMYPPPYF.VGMGNGTQiYvIDPEPC
hCTLA-4   LMYPPPYY.LGIGNGTQiYvIDPEPC
bCTLA-4   LMYPPPYY.VGMGNGTQiYvIEPEPC
  mCD28   FMYPPPYLDNERSNGTIiHIKEKHLC             Fig. 2
  rCD28   VMYPPPYLDNEKSNGTIiHiKEKHLC
  bCD28   VMYPPPYLDNEKSNGTIiHvKEQHFC
  hCD28   VMYPPPYLDNEKSNGTIiHvKEKHLC
  mICOS   IFDPPPFQER.NLSGGYlHiYESQLC
  hICOS   IFDPPPFK.V.TLTGGYlHiYESQLC
                120       130  136
```

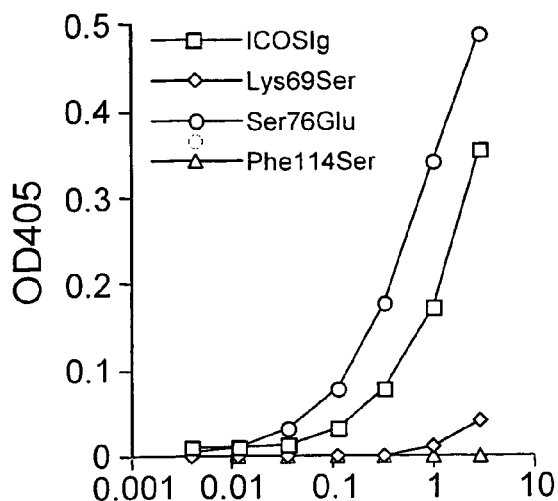
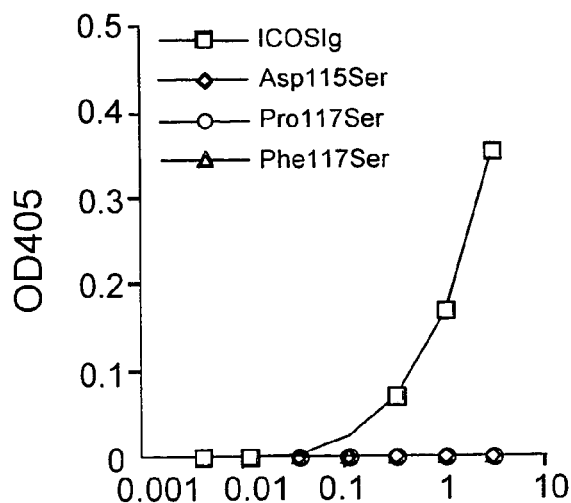
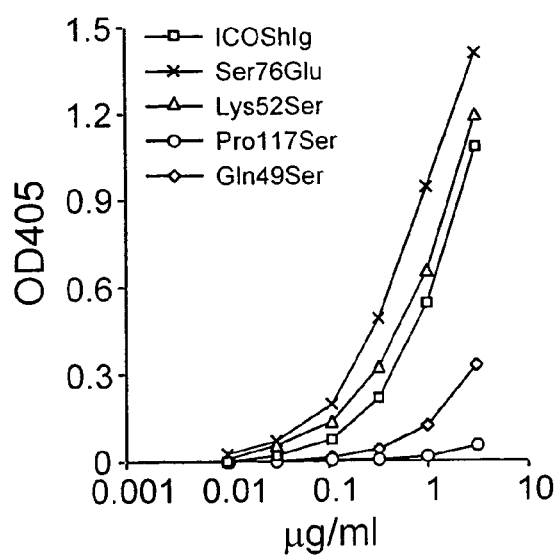

ICOS MUTANTS

TECHNICAL FIELD

This invention relates to T cell-mediated immune responses, and more particularly to compositions and methods for altering T cell-mediated immune responses.

BACKGROUND

Immune system responses are elicited in several different situations. The most frequent response involves protection against infectious microorganisms. An undesirable immune response can occur, however, following transplantation of foreign tissue, or in an autoimmune disease in which the body's own antigens become targets for the immune response. In order to initiate an antigen-specific response, a T cell must receive at least two discrete signals delivered by an antigen-presenting cell (APC). The first signal is antigen-specific, and is provided when the T cell receptor (TCR) interacts with an antigen in the context of a major histocompatibility complex (MHC) protein, or an MHC-related CD1 protein, that is expressed on the surface of an APC. The second, costimulatory, signal involves the interaction of a T cell surface antigen with its ligand on the APC. For example, the costimulatory molecule receptors CD28 and/or CTLA-4 (expressed on T cells) must interact with their ligands, B7-1 and/or B7-2 (expressed on APC), in order to achieve optimal activation of T cells that have been stimulated by MHC/peptide complexes expressed on APC. ICOS is an inducible T cell costimulatory receptor molecule that displays some homology to CD28 and CTLA-4, and interacts with B7-H2 expressed on the surface of APC. ICOS and B7-H2 have been implicated in the regulation of cell-mediated and humoral immune responses. Costimulatory molecules with altered binding affinities for their ligands would be useful for modulating the level of T cell activation and proliferation, and could be used either to boost the level of desired immune responses or to reduce the level of undesirable immune responses, as appropriate.

SUMMARY

The invention is based on the identification of key amino acid residues within the ICOS costimulatory receptor; these key residues affect the binding of ICOS to its ligand. The invention pertains to novel mutant forms of ICOS that modulate T cell activation and T cell-mediated immune responses. Such mutants are useful as therapeutic agents to manipulate T cell responses in vivo, so that desired immune responses are enhanced and undesirable immune responses are blocked.

In one aspect, the invention features a purified ICOS polypeptide having altered affinity for B7-H2 compared to a wild-type ICOS polypeptide, wherein the affinity is at least 6% of the affinity of the wild-type ICOS polypeptide. The purified ICOS polypeptide can differ from a wild-type ICOS polypeptide having the amino acid sequence of SEQ ID NO:12. The difference can be at amino acid position 76 (e.g., a glutamate at amino acid position 76) or at amino acid position 52 (e.g., a serine at amino acid position 52). The purified ICOS polypeptide can be capable of inhibiting T cell activation in a T cell proliferation assay.

In another aspect, the invention features an isolated nucleic acid molecule containing a nucleic acid sequence that encodes an ICOS polypeptide of the invention. The invention also features a vector containing the nucleic acid molecule of the invention. The nucleic acid contained within the vector can be operably linked to expression control sequences. The invention also features a host cell containing the vector.

In yet another aspect, the invention features a method for inhibiting T cell activation. The method can involve contacting an antigen-presenting cell with a purified ICOS polypeptide, wherein the polypeptide is capable of binding to B7-H2 with increased affinity relative to a wild-type ICOS polypeptide having the amino acid sequence of SEQ ID NO:12. The purified ICOS polypeptide can contain a Ser76Glu mutation or a Lys52Ser mutation.

The invention also features a method for inhibiting T cell activation in a subject. The method can involve administering an amount of a purified ICOS polypeptide that is capable of inhibiting a T cell response in the subject. The ICOS polypeptide can contain a Ser76Glu mutation or a Lys52Ser mutation. The subject can have an autoimmune disease (e.g., rheumatoid arthritis, systemic lupus erythematosus, or diabetes mellitus). The subject can be a transplant recipient.

In another aspect, the invention features a method for making an ICOS polypeptide. The method can involve culturing the cells of the invention and isolating the ICOS polypeptide from the culture.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a histogram showing the binding of human and mouse ICOSIg to human B7-H2. CHO cells were transfected with a human B7-H2 plasmid (open histograms) or vector control (shaded histogram), stained with human (right line) or mouse (left line) ICOSIg, and analyzed by flow cytometry.

FIG. 2 is a sequence alignment of the extracellular Ig-domains of mouse, rat, human, and bovine CTLA-4, mouse, rat, bovine, and human CD28, and mouse and human ICOS (SEQ ID NO:1 through SEQ ID NO:10, respectively; m, mouse; r, rat; h, human; b, bovine). β-strands observed in the solution structure of human CTLA-4 are labeled by letter; assignments of residues to the A and C" strands are tentative. Residue numbers are given for human ICOS. Ig V-set consensus residues and other hydrophobic core residues are shown in lower case. These are important for maintaining structural integrity but are not available for ligand binding. Other residues that are conserved in CD28, CTLA-4, and/or ICOS are shown in bold. Conservative residue replacements (e.g., Y/F, R/K, and E/Q) are taken into account. Residues that are conserved in CD28 and CTLA-4 and are critical for CD80/CD86 binding are labeled with asterisks. Potential N-linked glycosylation sites are boxed. The positions of ICOS residues subjected to site-specific mutagenesis are labeled with exclamation points.

FIGS. 3A, 3B, 3C, 3D, and 3E are line graphs depicting interactions between wild-type and mutant ICOSIg and B7-H2, as determined by ELISA. FIGS. 3A, 3B, 3C, and 3D show results obtained with ICOSIg polypeptides in concentrated supernatants from cultured COS cells, while FIG. 3E shows results obtained with purified ICOS proteins.

DETAILED DESCRIPTION

Figure 3A:
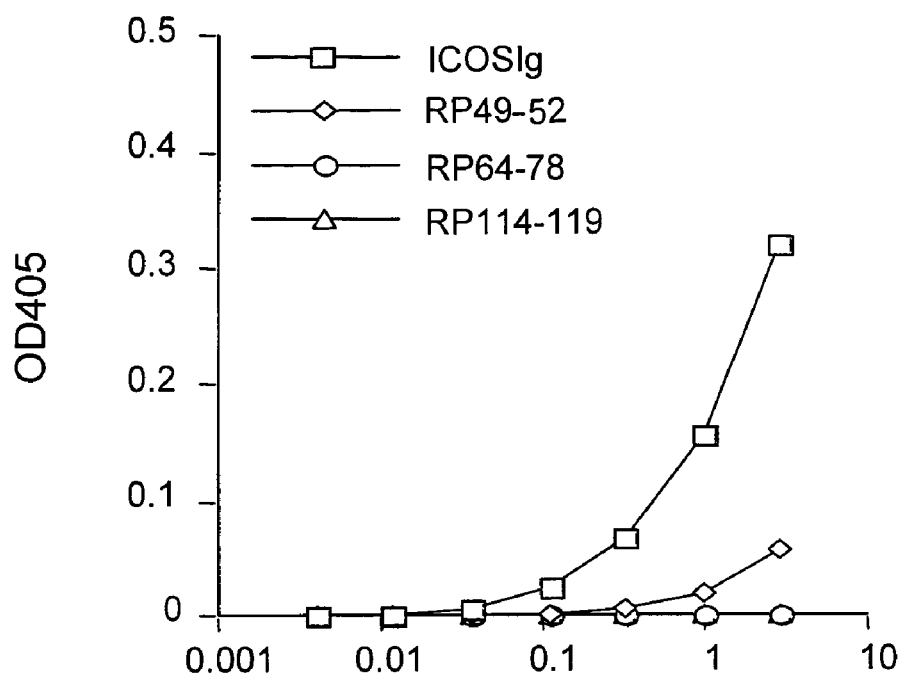

The receptor-ligand interactions of costimulatory molecules are required for optimal activation of T cells that have been stimulated by MHC/peptide complexes expressed on antigen-presenting cells (APC). T cell costimulatory proteins are members of the immunoglobulin (Ig) superfamily. For a discussion of the Ig superfamily, see Hunkapiller and Hood, *Adv. Immunol.* 44:1–63 (1989). Members of the family include the CD28 and CTLA-4 receptors, which are expressed on T cells, and their ligands, B7-1 and B7-2, which are expressed on APC. CD28 triggering increases antigen-specific proliferation of CD4$^+$ T cells, enhances production of cytokines, stimulates the effector function of CD8$^+$ T cells, and promotes T cell survival (Linsley and Ledbetter, *Annu. Rev. Immunol.* 11:191–192 (1993); Lenschow, Walunas, and Bluestone, *Annu. Rev. Immunol.* 14:233–258 (1996); Chambers and Allison, *Curr. Opin. Immunol.* 9:396–404 (1997); Boise, Noel, and Thompson, *Curr. Opin. Immunol.* 7:620–625 (1995); Rathmell and Thompson, *Annu. Rev. Immunol.* 17:781–828 (1999)). In contrast, signaling through CTLA-4 is thought to inhibit T cell proliferation, IL-2 production, and cell cycle progression (Krummel and Allison, *J. Exp. Med.* 183:2533–2540 (1996); Walunas, Bakker, and Bluestone, *J. Exp. Med.* 183:2541–2550 (1996)).

ICOS is a recently characterized member of the Ig superfamily (Hutloff et al., *Nature* 397:263–266 (1999); Buonfiglio et al., *Eur. J. Immunol.* 30:3463–3467 (2000)). Similar to CTLA-4, ICOS is induced upon T cell activation; CD28, on the other hand, is constitutively expressed on resting T cells. ICOS is structurally similar to both CD28 and CTLA-4; the overall length and relative position of the ICOS transmembrane domain are similar to those of CD28 and CTLA-4, and cysteine residues that are critical for the formation of intra- and inter-molecular disulfide bonds are conserved. CD28 and CTLA-4 each contain a single extracellular V-like Ig domain, which includes a strictly conserved MYPPPY motif (SEQ ID NO: 11) that is involved in ligand recognition (Peach et al., *J. Exp. Med.* 180:2049–2058 (1994)). While ICOS also contains a single extracellular Ig domain, the MYPPPY motif (SEQ ID NO:11) is not conserved—only the PPP portion of the hexapeptide motif is present.

Sequence alignment and molecular modeling revealed amino acid residues within ICOS that are likely to be involved in binding of ICOS to its ligand, B7-H2. The ligand binding domain thus was suggested to include the amino acid residues at positions 49–52, 64–68, 75–78, and 114–119 of SEQ ID NO:12 (all numbering of amino acid residues herein is with respect to SEQ ID NO:12, in which the initiator methionine is at position 1.) Mutation of these residues resulted in novel polypeptides with altered ligand binding affinities. Subsections below describe these polypeptides, nucleic acid molecules and host cells comprising sequences encoding the polypeptides, and methods for using the mutant polypeptides.

ICOS Polypeptides

The invention provides ICOS polypeptides containing the extracellular Ig-like domain. Such polypeptides typically will contain the ligand binding domain, and thus may contain amino acid positions that are important for ligand binding. An ICOS polypeptide of the invention can be from a human or a non-human (e.g., non-human primate, mouse, or rat) source. As used herein, "polypeptide" means any chain of amino acids, regardless of length or post-translational modification (e.g., phosphorylation or glycosylation). An "ICOS polypeptide" is any polypeptide that is at least 5 amino acids in length (e.g., 5, 6, 7, 8, 9, 10, 25, 50, or more than 50 amino acids in length), and has an amino acid sequence that is the same as, or substantially homologous to, the corresponding portion of the wild-type ICOS protein having the amino acid sequence of SEQ ID NO:12. An ICOS polypeptide can have a length that corresponds to that of the full length, wild-type ICOS protein, or can be shorter than the full length, wild-type protein (e.g., can be a truncated ICOS protein or can contain deletions relative to the full-length protein.) "Homologous," as used herein in reference to polypeptides, refers to the amino acid sequence similarity between two polypeptides. When an amino acid position in both of the polypeptides is occupied by identical amino acids, then they are homologous at that position. Thus, by a "substantially homologous polypeptide" is meant a polypeptide containing an amino acid sequence that is largely, but not entirely, homologous to the amino acid sequence of a reference polypeptide. As defined herein, a substantially homologous ICOS polypeptide has an amino acid sequence that is at least 75% (e.g., 80%, 85%, 90%, 95%, or 99%) homologous to the corresponding portion of the wild type ICOS polypeptide with the amino acid sequence of SEQ ID NO:12. Sequences that are substantially homologous can be identified by comparing the sequences using standard software that is frequently available in sequence data banks (e.g., the B12seq program.

Based on these definitions, ICOS polypeptides of the invention therefore may contain mutations relative to the wild-type ICOS protein. As used herein, "mutant ICOS polypeptide" means an ICOS polypeptide that includes any change (in comparison to the wild-type) in the amino acid sequence; such changes can originate within the DNA sequence encoding the polypeptide. Changes within the coding sequence can arise, for example, spontaneously, as a result of mating or other exchanging of genetic information, by genetic engineering, or by other forms of mutagenesis (e.g., by ultraviolet radiation). Mutations can include, for example, substitutions, deletions, insertions, inversions, translocations, or duplications. Substitutions may be conservative or non-conservative. Conservative amino acid substitutions replace an amino acid with an amino acid of the same class, whereas non-conservative amino acid substitutions replace an amino acid with an amino acid of a different class. Conservative substitutions typically have little effect on the overall structure or function of the polypeptide, and can include substitutions within the following groups: glycine and alanine; valine, isoleucine, and leucine; aspartic acid and glutamic acid; asparagines, glutamine, serine, and threonine; lysine, histidine, and arginine; and phenylalanine and tyrosine. Non-conservative substitutions may result in a substantial change in the hydrophobicity of the polypeptide or in the bulk of a residue side chain. In addition, non-conservative substitutions may make a substantial change in the charge of the polypeptide, such as reducing electropositive charges or introducing electronegative charges. Examples of non-conservative substitutions include a basic amino acid for a non-polar amino acid, or a polar amino acid for an acidic amino acid. Non-conservative substitutions are likely to have more significant effects on the function of the polypeptide (e.g., the ligand binding capability of ICOS).

Mutations within the ICOS polypeptide may be located in the ligand binding region. As used herein, a "ligand" is any protein or polypeptide that binds to a receptor protein or polypeptide. For example, the B7-H2 ligand binds to the T cell ICOS receptor protein and provides a costimulatory signal which, along with a first signal (e.g., a TCR/MHC signal), can result in T cell stimulation and activation. Mutations within the ICOS ligand binding region that result in altered affinity for B7-H2 (relative to wild type ICOS) are particularly useful. Typically, the mutant ICOS polypeptides of the invention bind to the B7-H2 ligand with an affinity that is increased or decreased by at least 10% (e.g., 10%, 20%, 30%, 50%, 75%, 100%, or more in the case of increased affinity), relative to the wild-type ICOS protein. Methods for measuring the relative binding affinity, such as capture ELISA and sandwich ELISA assays, are known in the art and are described in the Examples below.

Site-directed mutagenesis can be used to generate mutant forms of the ICOS polypeptide by introducing substitutions, deletions, or insertions into DNA sequences that encode the ICOS polypeptide. Methods of site-directed mutagenesis are well known in the art. For example, specific mutations can be generated by oligonucleotide-directed mutagenesis. In this method, a desired change is incorporated into a chemically synthesized oligonucleotide primer, which then is hybridized to a plasmid encoding a particular polypeptide of interest, in the presence of deoxynucleotides and a DNA polymerase. The primer is extended by the polymerase, creating a heteroduplex that contains a mismatch at the introduced change and a single-stranded nick at the 5' end. The nick can be sealed by DNA ligase and the plasmid can be transformed into *E. coli* or another suitable host, where the mismatch will be repaired. Alternatively, as described in the Example 1 (below), complementary oligonucleotides that both encode the desired change(s) can be used for PCR with flanking primers and an ICOS template (which for this method can be linear or circular, i.e., in a plasmid) to generate two products with an overlapping central region. These products can be used as templates in a second round of PCR along with the flanking primers, resulting in one product that contains the desired mutation(s). PCR methods are routine in the art and are described, for example, in *PCR Primer: A Laboratory Manual*, Dieffenbach and Dveksler, Eds., Cold Spring Harbor Laboratory Press, 1995. As another alternative, kits are available for site-directed mutagenesis. For example, Muta-Gene® in vitro mutagenesis kits are commercially available from Bio-Rad Laboratories (Hercules, Calif.), and the Transformer™ Site-Directed Mutagenesis kit is available from Clontech (Palo Alto, Calif.).

ICOS polypeptides containing mutations that are within the ligand binding region and that alter ligand binding affinity are particularly useful. Such mutations may involve more than one amino acid (e.g., amino acids 49 through 52, amino acids 64 through 78, or amino acids 114 through 119). Alternatively, a single amino acid may be mutated. For example, a mutant ICOS polypeptide containing a Glu at position 76 in place of the naturally occurring Ser is particularly useful. Such an ICOS polypeptide is referred to hereafter as the "Ser76Glu mutant," and is said to contain the "Ser76Glu mutation." Other useful mutations include, but are not limited to, Gln49Ser, Gln50Ser, Phe51 Ser, Lys52Ser, Asp64Ser, Lys67Ser, Lys69Ser, Phe114Ser, Asp115Ser, Pro117Ser, and Phe119Ser.

ICOS polypeptides of the invention may be modified for use in vivo by the addition, at the amino- or carboxy-terminal end, of a blocking agent to facilitate survival of the polypeptide in vivo. This can be useful in situations in which peptide termini tend to be degraded by proteases prior to cellular uptake. Such blocking agents can include, without limitation, additional related or unrelated peptide sequences that can be attached to the amino- and/or carboxy-terminal residues of the polypeptide. Such attachment can be achieved either chemically, during the synthesis of the polypeptide, or by recombinant DNA technology using methods familiar to those of ordinary skill in the art. Alternatively, blocking agents such as pyroglutamic acid or other molecules known in the art can be attached to the amino- and/or carboxy-terminal residues, or the amino group at the amino terminus or the carboxy group at the carboxy terminus can be replaced with a different moiety.

The ICOS polypeptides of the invention also can contain an amino acid tag. A "tag" is generally a short amino acid sequence that provides a ready means of detection or purification through interactions with an antibody against the tag or through other compounds or molecules that recognize the tag. For example, tags such as c-myc, hemagglutinin, polyhistidine, or Flag® can be used to aid purification and detection of a polypeptide. As an example, a polypeptide with a polyhistidine tag can be purified based on the affinity of histidine residues for nickel ions (e.g., on a Ni-NTA column), and can be detected in western blots by an antibody against polyhistidine (e.g., the Penta-His antibody; Qiagen, Valencia, Calif.). Tags can be inserted anywhere within the polypeptide sequence, although insertion at the amino- or carboxy-terminus is particularly useful.

The term "purified polypeptide" as used herein refers to a polypeptide that either has no naturally occurring counterpart (e.g., a peptidomimetic), or has been chemically synthesized and is thus uncontaminated by other polypeptides, or that has been separated or purified from other cellular components by which it is naturally accompanied (e.g., other cellular proteins, polynucleotides, or cellular components). Typically, the polypeptide is considered "purified" when it is at least 70%, by dry weight, free from the proteins and naturally occurring organic molecules with which it naturally associates. A purified polypeptide of the invention therefore can be, for example, at least 80%, at least 90%, or at least 99%, by dry weight, the polypeptide of the invention.

Methods for producing purified polypeptides are well known in the art. By way of example and not limitation, purified polypeptides can be obtained by extraction from a natural source (e.g., from isolated cells, tissues or bodily fluids), by expression of a recombinant nucleic acid encoding the peptide, or by chemical synthesis. Suitable methods for purifying the polypeptides of the invention can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

Expression vectors that encode ICOS polypeptides of the invention can be used to produce the ICOS polypeptides to be purified. Expression systems that can be used for small or large scale production of the polypeptide of the invention include, but are not limited to, microorganisms such as bacteria (e.g., *E. coli* and *B. subtilis*) transformed with recombinant bacteriophage DNA, plasmid DNA, or cosmid DNA expression vectors containing the nucleic acid molecules of the invention; yeast (e.g., *S. cerevisiae*) transformed with recombinant yeast expression vectors containing the nucleic acid molecules of the invention; insect cell systems infected with recombinant virus expression vectors (e.g., baculovirus) containing the nucleic acid molecules of the invention; plant cell systems infected with recombinant virus expression vectors (e.g., tobacco mosaic virus) or transformed with recombinant plasmid expression vectors (e.g., Ti plasmid) containing the nucleic acid molecules of the invention; or mammalian cell systems (e.g., primary cells or immortalized cell lines such as COS cells, CHO cells, He La cells, HEK 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids of the invention.

The invention also provides peptidomimetic compounds that are designed on the basis of the amino acid sequences of ICOS polypeptides. Peptidomimetic compounds are synthetic compounds having a "peptide motif," which as used herein refers to a three-dimensional conformation that is substantially the same as the three-dimensional conformation of a selected peptide, and can thus confer the same or similar function as the selected peptide. For example, an ICOS peptidomimetic compound with the same three-dimensional conformation as the wild-type ICOS protein could function as a receptor for T cell costimulation in a manner analogous to that of the wild-type ICOS protein. In another example, an ICOS peptidomimetic compound with the same or similar three-dimensional conformation as the ligand binding domain of the wild-type ICOS protein could interact with B7-H2 to inhibit T cell proliferation. Peptidomimetic compounds of the invention can be designed to mimic any of the ICOS polypeptides of the invention.

Peptidomimetic compounds that are protease resistant are particularly useful. Furthermore, peptidomimetic compounds may have additional characteristics that enhance therapeutic utility, such as increased cell permeability and prolonged biological half-life. Such compounds typically have a backbone that is partially or completely non-peptide, but with side groups that are identical to the side groups of the amino acid residues that occur in the peptide upon which the peptidomimetic compound is based. Several types of chemical bonds (e.g., ester, thioester, thioamide, retroamide, reduced carbonyl, dimethylene and ketomethylene) are known in the art to be useful substitutes for peptide bonds in the construction of peptidomimetic compounds.

Nucleic Acids

The invention provides isolated nucleic acid molecules that encode ICOS polypeptides. As used herein, "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). The term "isolated" as used herein with reference to a nucleic acid refers to a naturally-occurring nucleic acid that is not immediately contiguous with both of the sequences with which it is immediately contiguous (one at the 5' end and one at the 3' end) in the naturally-occurring genome of the organism from which it is derived. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences that is normally immediately contiguous with the DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Isolated nucleic acids of the invention contain sequences encoding the ICOS polypeptides of the invention, and thus typically correspond to sequences that encode amino acids from the extracellular Ig domain of an ICOS polypeptide from a human or non-human (e.g., non-human primate, mouse, or rat) source. The nucleic acids may contain sequences identical to those encoding a wild-type ICOS polypeptide. Alternatively, the nucleic acids can contain codons other than the wild-type codons which, due to the degeneracy of the genetic code, encode ICOS polypeptides identical to the wild-type polypeptide. Furthermore, the nucleic acids may encode ICOS polypeptides with any of the mutations described above (i.e., substitutions, deletions, insertions, duplications, inversions, and transpositions).

Nucleic acids of the invention may contain coding sequences for ICOS polypeptides coupled to sequences that encode one or more additional polypeptides or tags. Furthermore, the coding sequences can be linked in frame and inserted into a suitable expression vector, such that one polypeptide results from transcription and translation of the coding sequences. For example, the nucleic acids of the invention may include coding sequences from both ICOS and Ig, linked in such a way that a single ICOSIg polypeptide is produced. Additionally, nucleic acids of the invention can encode ICOS polypeptides coupled to one or more suitable tags such as those described above.

The invention also provides vectors containing the nucleic acids described above. As used herein, a "vector" is a replicon, such as a plasmid, phage, or cosmid, into which another DNA segment may be inserted so as to bring about the replication of the inserted segment. The vectors of the invention are preferably expression vectors, in which the nucleotides encode the ICOS polypeptides of the invention with an initiator methionine, operably linked to expression control sequences. As used herein, "operably linked" means incorporated into a genetic construct so that expression control sequences effectively control expression of a coding sequence of interest. An "expression control sequence" is a DNA sequence that controls and regulates the transcription and translation of another DNA sequence, and an "expression vector" is a vector that includes expression control sequences, so that a relevant DNA segment incorporated into the vector is transcribed and translated. A coding sequence is "operably linked" and "under the control" of transcriptional and translational control sequences in a cell when RNA polymerase transcribes the coding sequence into mRNA, which then is translated into the protein encoded by the coding sequence.

Methods well known to those skilled in the art may be used to subclone isolated nucleic acid molecules encoding polypeptides of interest into expression vectors containing relevant coding sequences and appropriate transcriptional/translational control signals. See, for example, Sambrook et al., *Molecular Cloning: A Laboratory Manual (2$^{nd}$ edition)*, Cold Spring Harbor Laboratory, New York (1989); and Ausuble et al., *Current Protocols in Molecular Biology*, Green Publishing Associates and Wiley Interscience, New York (1989). Expression vectors of the invention can be used in a variety of systems (e.g., bacteria, yeast, insect cells, and mammalian cells), as described above. Examples of suitable expression vectors include, without limitation, plasmids and viral vectors derived from, for example, herpes viruses, retroviruses, vaccinia viruses, adenoviruses, and adeno-associated viruses. A wide variety of suitable expression vectors and systems are commercially available, including the pET series of bacterial expression vectors (Novagen, Madison, Wis.), the Adeno-X expression system (Clontech), the Baculogold baculovirus expression system (BD Biosciences Pharmingen, San Diego, Calif.), and the pCMV-Tag vectors (Stratagene, La Jolla, Calif.).

Host Cells and Non-Human Transgenic Animals

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., above, and reagents for transformation and/or transfection are commercially available (e.g., Lipofectin (Gibco/BRL, Gaithersburg, Md.), Fugene (Roche, Indianapolis, Ind.), and SuperFect (Qiagen)).

Host cells of the invention can be used to produce the ICOS polypeptides of the invention. For example, bacteria transformed with an ICOS expression vector can be induced to express the ICOS polypeptide encoded by the vector, and the polypeptide of interest can be subsequently purified from bacterial lysates by methods described above. ICOS polypeptides also can be purified from lysates of mammalian host cells transfected with ICOS expression vectors of the invention. Alternatively, as described in Example 1 (below), mammalian cells transfected to express ICOS may secrete the polypeptides into their culture media, from which the ICOS polypeptides can be recovered.

The isolated nucleic acids and host cells of the invention also can be used to generate non-human transgenic animals. As used herein, a "transgenic animal" is an animal that includes a transgene that is inserted into an embryonal cell and becomes a part of the genome of the animal that develops from that cell, or an offspring of such an animal. A "transgene" refers to an isolated nucleic acid that encodes a polypeptide of interest and is introduced into a cell or an organism where it is not naturally found. The term "transgene" thus can include mutated versions of genes that would not normally be found in the transgenic cells. The term "embryonal cell" includes primordial germ cells, fertilized oocytes, and embryonal stem cells. In the transgenic animals described herein, a transgene may encode an ICOS polypeptide that includes the Ig-like extracellular domain thought to be responsible for ligand binding, and that may have altered affinity for B7-H2 if one or more mutations are present. Vectors containing coding sequences for ICOS polypeptides that are operably linked to a T cell specific promoter are particularly useful. Transgenic animals generated with such vectors would express mutant forms of ICOS specifically in their T cells.

Typically, transgenic non-human animals are mice, but other animals (e.g., rats, rabbits, or fish) also may be used. Methods for creating such transgenic animals are well known in the art. A transgenic animal can be generated, for example, by introducing (e.g., by microinjection) a nucleic acid encoding a polypeptide of interest into the male pronucleus of a fertilized oocyte, and allowing the oocyte to develop in a pseudopregnant female foster animal. A transgenic animal (e.g., a mouse) that expresses a mutant ICOS polypeptide of the invention therefore can be created by introducing an isolated nucleic acid encoding the ICOS Ser76Glu mutant. Intronic sequences and polyadenylation signals also can be included in a transgene to increase the efficiency of transgene expression. As described above, the isolated nucleic acids can be linked to regulatory sequences that control transcription and translation and can limit expression of the encoded protein to one or more specific cell types. Transgenic founder animals can be bred to generate additional animals carrying the transgene. Further discussion of methods for creating transgenic animals, particularly mice, can be found in Hogan et al., A Laboratory Manual, Cold Spring Harbor Laboratory, New York (1986); and U.S. Pat. Nos. 4,736,866 and 4,870,009.

The isolated nucleic acids of the invention can be used to create non-human homologous recombinant animals. As used herein, the term "homologous recombinant animal" is intended to describe an animal containing a gene that has been modified by homologous recombination. Typically, homologous recombinant non-human animals are mice, although other animals (e.g., rats or rabbits) also may be used. A homologous recombination event may completely disrupt the endogenous gene such that a functional gene product can no longer be produced (resulting animals often are referred to as "knock-out" animals). Alternatively, a homologous recombination event can modify a gene such that an altered gene product is produced. For example, an isolated nucleic acid of the invention can be used to create a homologous recombinant mouse in which a recombination event has occurred in the ICOS gene, such that an exon encoding the B7-H2 binding domain is altered. Isolated nucleic acids encoding the mutant ICOS polypeptides disclosed above (e.g., the Ser76Glu ICOS mutant or the Lys52Ser ICOS mutant) are particularly useful. Transgenic animals can be bred to generate additional animals carrying such a homologously recombined transgene, and animals that are homozygous for the newly introduced transgene would express only the mutant form of ICOS.

Methods for generating homologous recombinant animals are well known in the art. To create such animals, for example, a vector can be designed to contain the nucleic acids that are to replace the endogenous DNA sequences, flanked by DNA sequences that are homologous to the endogenous flanking sequences (see, for example, Thomas and Capecchi, *Cell* 51:503–512 (1987)). The vector can be introduced into an embryonic stem cell line (e.g., by electroporation) and cells in which the introduced DNA has homologously recombined with the endogenous DNA can be selected (see Li et al., *Cell* 69:915–926 (1992)). The selected cells then can be injected into a blastocyst of an animal (e.g., a mouse) to form aggregation chimeras (see, for example, Bradley, pp. 113–152 in *Teratocarcinomas and Embryonic Stem Cells: A Practical Approach*, IRL, Oxford (1987)). Chimeric embryos then can be implanted into suitable pseudopregnant female foster animals and brought to term. Progeny harboring the homologously recombined DNA in their germ cells may be used to breed animals in which all cells of the animal contain the homologously recombined DNA.

Methods for Using ICOS Polypeptides, Nucleic Acids, and Host Cells

ICOS polypeptides, vectors, and host cells of the invention can be administered to a cell population in order to modulate T cell responses. For example, mutant ICOS polypeptides with enhanced affinity for B7-H2 can be administered as therapeutic agents when it is desired to inhibit T cell activation and proliferation. As disclosed in the Examples below, immobilized B7-H2 can costimulate T cell proliferation, and a purified ICOS polypeptide was able to block that costimulatory effect. As used herein, a mutant ICOS polypeptide that can "inhibit" T cell activation refers to a polypeptide that can decrease T cell proliferation to an extent that is at least 10% (e.g., 10%, 20%, 50%, 75%, 100%, or more) greater than the decrease achieved by the wild type ICOS polypeptide as measured by the T cell proliferation assay set forth in Example 1, below. The Ser76Glu and Lys52Ser mutant ICOS polypeptides are particularly useful.

ICOS polypeptides can be administered either in vitro or in vivo. In one embodiment, ICOS polypeptides of the present invention can be administered to target cells derived from tumors or to freshly isolated cells such as, for example, peripheral blood mononuclear cells (PBMC) or T cells. Through such an in vitro approach, various mutant ICOS polypeptides can be evaluated before they are used for in vivo approaches. Methods of quantifying the B7-H2 binding avidity of a polypeptide are known in the art, as are methods of measuring a polypeptide's effect on T cell responses (e.g., as in Example 1).

In another embodiment, mutant ICOS polypeptides can be incorporated into pharmaceutical compositions and administered to a subject that exhibits or is at risk for an undesirable immune response. Undesirable immune responses include, for example, immune responses against foreign tissues following transplantation (e.g., kidney, liver, lung, heart, bone marrow, or stem cell transplantation), and immune responses in autoimmune diseases in which the body's own antigens become targets for an immune response (e.g., rheumatoid arthritis, multiple sclerosis, or insulin dependent diabetes mellitus). ICOS polypeptides of the invention may be administered prophylactically, such as to a transplant recipient in order to guard against graft rejection. The Ser76Glu and Lys52Ser mutant ICOS polypeptides are particularly useful.

Generally, pharmaceutical compositions of the invention contain one or more ICOS polypeptides suspended in a pharmaceutically acceptable carrier. A "pharmaceutically acceptable carrier" is a pharmaceutically acceptable solvent, suspending agent, or any other pharmacologically inert vehicle for delivering one or more therapeutic compounds (e.g., ICOS polypeptides) to a subject. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

ICOS polypeptides of the invention can be administered orally or by intravenous infusion, or injected (e.g., subcutaneously, intramuscularly, or intraperitoneally). The dosage required will depend on the route of administration, the nature of the composition, the nature of the subject's illness, and the subject's size, weight, surface area, age, and sex, other drugs being administered, and the judgment of the attending physician. Wide variations in the necessary dosage are to be expected in view of the differing efficiencies of various routes of administration. For example, oral administration would be expected to require higher dosages than administration by injection. Variations in these dosage levels can be adjusted using standard empirical routines for optimization as is well understood in the art. Generally, doses of an ICOS polypeptide administered to a subject are adjusted such that the amount provided decreases T cell proliferation to an extent that is at least 10% (e.g., 10%, 20%, 50%, 75%, 100%, or more) greater than the decrease achieved by the wild type ICOS polypeptide as measured by the T cell proliferation assay set out in Example 1, below.

In another embodiment, vectors of the invention (e.g., expression vectors containing ICOS nucleic acids linked to expression control sequences) can be transfected or transformed into host cells in vitro to produce ICOS polypeptides. Alternatively, such vectors can be administered to a subject that exhibits or is at risk for an undesirable immune response. Examples of such undesirable immune responses are provided above. In yet another embodiment, host cells transfected ex vivo with a vector of the invention can be returned to the subject in order to inhibit a T cell response. Vectors containing the nucleic acids encoding the Ser76Glu or Lys52Ser mutant ICOS polypeptides, and host cells containing such vectors, are particularly useful in these embodiments.

Articles of Manufacture

ICOS polypeptides of the invention can be combined with packaging material and sold as kits for moderating immune responses. Components and methods for producing articles of manufacture such as kits are well known. An article of manufacture may include one or more of the ICOS polypeptides set out in the above sections. In addition, the article of manufacture further may include buffers or other solutions necessary to effect modulation of an immune response. Instructions describing how the ICOS polypeptides are useful for moderating immune responses can be included in such kits.

Alternatively, an article of manufacture can contain an ICOS nucleic acid (e.g., a vector containing a nucleic acid sequence encoding a mutant ICOS polypeptide, operably linked to expression control sequences). Such an article of manufacture can include instructions for using the ICOS nucleic acids to produce a mutant ICOS polypeptide, as well as any components necessary to achieve such production. In another embodiment, an article of manufacture can contain host cells that contain ICOS nucleic acids, which are useful for producing ICOS polypeptides.

The invention will be further described in the following examples, which do not limit the scope of the invention described in the claims.

EXAMPLES

Example 1

Materials and Methods

Cell culture: Stably transfected B7-H2$^+$ Chinese hamster ovary (CHO) cells were maintained in CHO-SF II medium (Gibco BRL, Gaithersburg, Md.) supplemented with 10% heat-inactivated fetal bovine serum (FBS; HyClone, Logan, Utah). COS cells were cultured in Dulbecco's Modified Eagle Medium (DMEM; Gibco BRL) supplemented with 10% FBS, 25 mM HEPES, 2 mM L-glutamine, 1 mM sodium pyruvate, 1% MEM nonessential amino acids, and 100 U/ml penicillin G and 100 µg/ml streptomycin sulfate.

Ig-Fusion proteins: The fusion proteins with the extracellular domain of human B7-H2 linked to either mouse IgG2a or the human IgG1 Fc portion (B7-H2Ig) were produced in stably transfected B7-H2$^+$ CHO cells and purified as previously described (Lucia et al., *AIDS Res. Hum. Retroviruses* 16:549–557 (2000)). ICOSIg was produced by transiently transfecting COS cells with a plasmid created by fusing cDNA sequences encoding the extracellular domain of human ICOS in frame to the CH2-CH3 portion of human IgG1 (Dong et al., *Nature Med.* 12:1365–1369 (1999)). Transfected COS cells were cultured in serum-free DMEM, and concentrated culture supernatants were used as sources of the Ig fusion proteins. Ig fusion proteins also were purified as previously described (Lucia et al., supra).

Residue mapping: The solution structure of the monomeric extracellular Ig V-like domain of CTLA-4 (Metzler et al., *Nat. Struct. Biol.* 4:527–531 (1997)), and molecular models of human CD28 (Bajorath, Metzler and Linsley, *J. Mol. Graph. Model.* 15:135–139 (1997)) and human ICOS (Bajorath, *J. Mol. Model.* 5:169–176 (1999)) were used to study residue conservation in human and house ICOS relative to CTLA-4 and CD28. Computer graphical analysis was carried out using InsightII (MSI, San Diego, Calif.).

ICOSIg mutants: Based on sequence alignment and residue mapping, selected regions and residues of ICOS were mutagenized either by homologous replacement or by point mutation. Homologue replacement mutant plasmids were designed to replace regions of ICOS that appeared to be important for ligand binding with the corresponding portions of CD28. All ICOSIg mutants were constructed by two-step PCR using ICOSIg cDNA as the template. Overlapping oligonucleotide primers were synthesized to encode the desired mutations (as shown in Table 1 and Table 2), and flanking 5' and 3' primers were designed to contain EcoRI and BglII restriction sites, respectively. Appropriate regions of the cDNA were initially amplified using the corresponding overlapping and flanking primers. Subsequently, the two fragments with overlapping sequences were linked by PCR using the flanking 5' and 3' primers. PCR products were digested with EcoRI and BglII and ligated into EcoRI/BglII-digested pHIg vectors (Lucia et al., supra). To verify that the desired mutations were introduced, each construct was sequenced using an ABI Prism 310 Genetic Analyzer (Applied Biosystems, Foster City, Calif.). The plasmids were transfected into COS cells and serum-free supernatants were harvested and used as sources of Ig fusion proteins. For some experiments, the Ig fusion proteins also were purified on a protein G affinity column as previously described (Lucia et al., supra).

TABLE 1

Primers used to generate homologue replacement mutants

| Primer | Sequence (5'→3') | SEQ ID NO |
|---|---|---|
| RP49-52 5' | TTATGCAAATATCCTGACATTGTCAGGGAGTTCCGGATGCAGTTGCTGAAAGGGGGCAAAT | 13 |
| RP49-52 3' | GACAATGTCAGGATATTTGCAT | 14 |
| RP64-78 5' | TTACTCCCAGCAGCTTCAGGTTTACTCAAAAAGTCTGAAATTCTGCCATTCTCAGTTAT | 15 |
| RP64-78 3' | TAAACCTGAAGCTGCTGGGAGTAATTCCCATATACAACGCAGAGTATTTGCCCCCCTTTCAGCAAC | 16 |
| RP114-119 5' | TATTACTTCTGCAACCTATCAATTGCTGCTCCTCCTCCTTTT | 17 |
| RP114-119 3' | AGCAATTGATAGGTTGCAGAAGT | 18 |

TABLE 2

Primers used to generate point mutations

| Mutant | 5'primer (5'→3') | SEQ ID NO | 3'primer (5'→3') | SEQ ID NO |
|---|---|---|---|---|
| Gln49Ser | CCTGACATTGTCTCGCAATTTAAAATGCAG | 19 | CTGCATTTTAAATTGCGAGACAATGTCAGG | 20 |
| Gln50Ser | CCTGACATTGTCCAGTCATTTAAAATGCAG | 21 | CTGCATTTTAAATGACTGGACAATGTCAGG | 22 |
| Phe51Ser | GTCCAGCAATCTAAAATGCAG | 23 | CTGCATTTTAGATTGCTGGAC | 24 |
| Lys52Ser | GTCCAGCAATTTAGCATGCAGTTGCTG | 25 | CAGCAACTGCATGCTAAATTGCTGGAC | 26 |
| Asp64Ser | GGCAAATACTCTGCTCTCTCACTAAGACAAAAGG | 27 | CCTTTTGTCTTAGTGAGAGAGCAGAGTATTTGCC | 28 |
| Lys67Ser | CTGCGATCTCACTAGCACAAAAGGAAGTGG | 29 | CCACTTCCTTTTGTGCTAGTGAGATCGCAG | 30 |
| Lys69Ser | GCGATCTCACTAAGACAAGCGGAAGTGG | 31 | CCACTTCCGCTTGTCTTAGTGAGATCGC | 32 |
| Ser76Glu | GTGGAAACACAGTGGAAATTAAGAGTCTG | 33 | CAGACTCTTAATTTCCACTGTGTTTCCAC | 34 |
| Phe114Ser | CCTATCAATTTCTGATCCTCCTCC | 35 | GGAGGAGGATCAGAAATTGATAGG | 36 |
| Asp115Ser | CCTATCAATTTTTTCTCCTCCTCC | 37 | GGAGGAGGAGAAAAAATTGATAGG | 38 |
| Pro117Ser | CAATTTTTGATCCTTCTCCTTTTAAAG | 39 | CTTTAAAAGGAGAAGGATCAAAAATTG | 40 |
| Phe119Ser | CCTCCTCCTTCTAAAGTAACTCTTACAG | 41 | CTGTAAGAGTTACTTTAGAAGGAGGAGG | 42 |

ELISA: To quantitate Ig fusion proteins in culture media, microtiter plates were coated with 2 μg/ml goat anti-human IgG (Sigma, St. Louis, Mo.). After an overnight incubation at 4° C., wells were blocked for 1 hour with blocking buffer (10% FBS in PBS) and then washed with PBS containing 0.05% Tween 20 (PBS-Tween). Aliquots of COS cell culture media supernatants were added, and the plates were incubated for 2 hours at room temperature. Known concentrations of ICOSIg were added to separate wells on each plate for the generation of standard curves. After washing, horseradish peroxidase (HRP)-conjugated goat anti-human IgG (TAGO, Inc., Burlingame, Calif.) diluted at 1:2000 was added to each well, and plates were incubated for 1 hour at room temperature. Wells were then washed and incubated with 3,3',5,5' tetramethylbenzidine (TMB) substrate for 5 to 15 minutes, at which point the reaction was stopped by the addition of 0.5 M $H_2SO_4$. Absorbances were measured at 405 nm on a microtiter plate reader. Concentrations of mutant fusion proteins were determined by comparison with the standard curve generated by the ICOSIg controls. Data from triplicate wells were assessed, and standard deviations from the mean were <10%. Each experiment was repeated at least three times.

The ability of ICOSIg mutants to bind B7-H2 was measured using capture ELISA. Recombinant B7-H2mIg fusion proteins were coated on microtiter plates at 5 μg/ml and incubated overnight at 4° C. As described above, wells were blocked and then washed with PBS-Tween, and COS cell culture media was added and incubated for 2 hours at room temperature. HRP-conjugated goat anti-human IgG was added after washing, followed by TMB substrate and $H_2SO_4$, and absorbance was measured at 405 nm.

Flow cytometry: B7-H2$^+$ CHO cells ($1\times10^5$ cells per sample) were incubated on ice for 45 minutes, in a 1:1 mixture of fluorescence activated cell sorter (FACS) buffer (3% FBS and 0.02% $NaN_3$ in PBS):COS cell culture media containing ICOSIg fusion proteins. The B7-H2Ig fusion protein was used as a negative control. The cells were washed and further incubated with fluorescein isothiocyanate (FITC)-conjugated goat anti-human IgG (BioSource, Camarillo, Calif.) on ice for 30 minutes. Fluorescence was analyzed on a FACScaliber flow cytometer (Becton Dickinson, Mountain View, Calif.) with Cell Quest software (Becton Dickinson).

Surface plasmon resonance analysis: All experiments were performed on a BIAcore™ 3000 instrument (Biacore, Piscataway, N.J.) at 25° C. using running buffer containing 0.1 M HEPES pH 7.4, 0.15 M NaCl, and 0.005% surfactant P20. B7-H2Ig fusion protein was covalently coupled by primary amine groups to the carboxymethylated dextran matrix on a CM5 sensor chip (Biacore) via random amine coupling chemistry. The dextran surface was activated with N-ethyl-N-dimethylaminopropyl carbodiimid/N-hydroxysuccinimide, followed by injection of 20 μg/ml B7-H2Ig protein diluted in 10 mM sodium acetate buffer (pH 4.5). The protein was exposed to the activated surface until 3800 response units (RU) was observed. The excess active groups on the dextran were blocked with 1 M ethanolamine. A control sensor surface was prepared by activating and blocking a separate flow cell without protein immobilization. Wild type ICOSIg and ICOSIg mutants were diluted to 500 nM in running buffer and injected across the immobilized surfaces at a flow rate of 30 μl/min for 2.66 minutes. Data were analyzed performed using the BIAevaluation software Version 3.2 (Biacore).

T cell proliferation assays: Enrichment of T cells was performed by passing nonadherent peripheral blood mononuclear cells from a healthy donor through nylon wool columns (Robbins Scientific Co., Sunnyvale, Calif.) as described previously (Lucia et al., supra). For the T cell proliferation assay, flat-bottomed 96-well microplates were coated with 50 μl of anti-CD3 mAb (5 ng/ml; BD Pharmingen, San Diego, Calif.) and incubated overnight at 4° C. After intensive washing with PBS, the plates were further coated with 50 μl of B7-H2Ig (5 μg/ml) and incubated at 37° C. for 2 hours. Purified T cells ($2\times10^5$ cells per well) were added along with various amounts of either the Ser76Glu mutant protein or ICOSIg. Each sample was done in triplicate. Cells were cultured for 72 hours; [$^3$H]-thymidine (Amersham Pharmacia Biotech, Piscataway, N.J.) was added at 1.0 µCi/well during the last 9 hours of incubation. Cells were vacuum-harvested onto glass fiber filters, which were dried and immersed in scintillation fluid, and the incorporation of [$^3$H]-thymidine was assessed in a Micro-Beta Trilux liquid scintillation counter (Wallac, Turku, Finland).

Adherent cells were prepared for allogeneic mixed lymphocyte reactions (MLR) by incubation of purified PBMC from healthy donors in plastic dishes. MLR were set up by co-culturing 1×10$^5$ gamma-irradiated adherent cells (3000 rad $^{137}$Cs) with 2×10$^5$ purified allogeneic T cells in the presence of various concentrations of Ser76Glu mutant protein and ICOSIg. The cells were co-cultured in 96-well round-bottom microtiter plates for 5 days. T cell proliferation was assessed as described above, after the addition of 1 µCi/well [$^3$H]-thymidine for the final 9 hours of incubation.

Example 2

Binding and Sequence Analysis of Human and Mouse ICOS

Cross species binding of ICOS and B7-H2 ligand: Previous studies have demonstrated that murine B7RP-1 binds to human ICOS (Yoshinaga et al., *Int. Immunol.* 12:1439–1447 (2000)), suggesting that human and mouse ICOS have cross-species binding capability. To investigate this possibility, a vector encoding human B7-H2 (Wang et al., *Blood* 96:2808–2813 (2000); SEQ ID NO:43) was transfected into CHO cells, and the cells were stained with either human or mouse ICOSIg. FACS analysis showed that both human and mouse ICOSIg could interact with B7-H2, although mouse ICOSIg bound less well than its human counterpart (FIG. 1). This suggested that the ligand binding sites in human and mouse ICOS are conserved and that similar residues contribute to the binding of B7-H2 ligand.

Sequence analysis and molecular models of ICOS: A sequence-structure comparison of ICOS and CD28/CTLA-4 was conducted to test the hypothesis proposed above. An alignment of extracellular Ig-domain sequences from the extended CD28 family is shown in FIG. 2. Although the region corresponding to the "MYPPPY" motif (SEQ ID NO:11) in CD28 and CTLA-4 (which is critical for B7 binding and function of these proteins) is most conserved within the extended CD28 family, only the PPP sequence is conserved in human and mouse ICOS. Human and mouse ICOS do, however, share a number of conserved residues with CD28 and/or CTLA-4. In addition, the alignment revealed other regions of ICOS-specific residue conservation. Since ICOS exhibits cross-species ligand binding (FIG. 1, above), such conserved residue segments are likely to determine the binding specificity of the protein.

To project residue conservation into three dimensions, residues that are conserved in the CD28 family were mapped on the solution structure of human CTLA-4 and on molecular models of human CD28 and human ICOS that were generated based on the CTLA-4 structure. The analysis suggested that both CD28/CTLA-4-specific and ICOS-specific residue conservation is concentrated on the upper part of the A 'GFCC' face of the domain, proximal to the conserved "MYPPPY" (SEQ ID NO:11) or "PPP" motifs. Some residue conservation also was observed on the opposite (BED) face of the domain. This region is not likely to be available for ligand binding however, as it is masked by N-linked glycosylation sites in ICOS and CD28. By contrast, there are no glycosylation sites within the conserved regions on the A 'GFCC' face of the domain. In the ICOS model, the spatially continuous region of conserved residues is essentially formed by four discontinuous sequence segments: amino acids 49 to 52, 64 to 68, 75 to 78, and 114 to 119. These conserved regions are likely to play an important role in ligand binding by ICOS.

Example 3

Analysis of ICOS Mutants

Mutagenesis analysis of the interaction between ICOS and B7-H2: The conserved regions within ICOS were subjected to mutagenesis in order to analyze their importance for binding to B7-H2. As a first step, the discontinuous sequence segments that contribute to the formation of the conserved surface patch of human ICOS (above) were replaced by corresponding regions of human CD28. The segments spanning amino acids 64 to 68 and 75 to 78 were combined, so that a total of three homologue replacement mutants were generated (RP49–52, RP64–78, and RP114–119). These constructs were expressed as ICOSIg hybrid proteins in COS cells, and the concentrations of the mutant proteins in serum-free culture media was determined by sandwich ELISA using anti-human Ig mAbs (BD Pharmingen). All three mutant hybrid proteins were successfully expressed, as they were bound by ICOS antiserum at levels comparable to wild-type ICOSIg. The ability of each ICOSIg mutant to bind to B7-H2 was determined by sandwich ELISA using B7-H2Ig (mouse Ig) and anti-human Ig mAb (FIG. 3A), and also by FACS analysis of ICOSIg binding to CHO cells that were transfected to express B7-H2. Similar results were obtained by both methods. As summarized in Table 3, mutant RP49–52 bound to B7-H2 but at a considerably lower level than wild-type ICOSIg, while the mutants RP64–78 and RP114–119 displayed a complete loss of binding. Since all three mutants showed either significantly reduced or completely abolished binding to B7-H2, residues within the mutagenized regions are very likely involved in ligand binding either directly (i.e., as contact residues) or indirectly (i.e., acting to maintain local structural integrity).

Figure 3B:
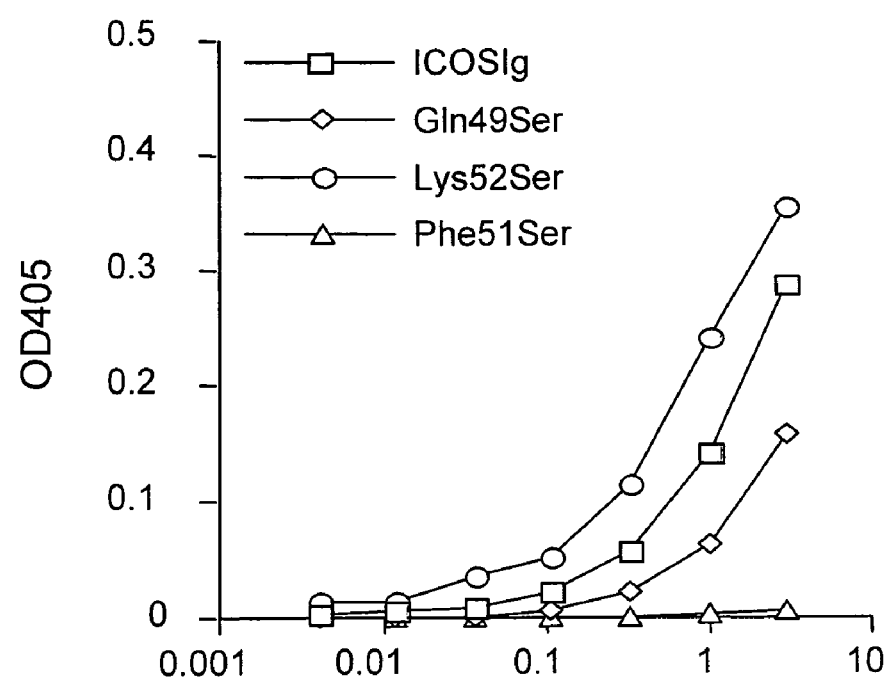

In the second step of the mutagenic analysis, the importance of individual amino acids was examined. The residues selected for mutagenesis all mapped to positions on the surface of the molecular model (and thus were predicted to be available for ligand binding); four residue-specific mutants were generated within each of the three targeted regions. The majority of the selected residues were mutated to serine, which is more polar than alanine and therefore more compatible with solvent-exposed positions. Expression plasmids encoding the ICOSIg mutants were transfected into COS cells, and the resulting ICOSIg mutant polypeptides (either in concentrated media supernatants or purified from the culture media) were tested by capture ELISA for binding to B7-H2Ig. The results of these experiments are summarized in Table 3. The mutants fell into four basic classes as compared to wild-type ICOSIg. Gln49Ser displayed slightly reduced binding to B7-H2Ig (FIGS. 3B and 3E); Gln50Ser, Asp64Ser, and Lys69Ser exhibited a more severe loss of binding (FIG. 3C); and Phe51Ser, Lys67Ser, Phe114Ser, Asp115Ser, Pro117Ser, and Phe119Ser showed no binding to B7-H2Ig (FIGS. 3B, 3C, 3D, and 3E). In contrast, Lys52Ser and Ser76Glu bound B7-H2Ig to an extent that was two- to three-fold higher than wild-type ICOSIg, as determined by the linear portions of the respective binding curves generated by ELISA (FIGS. 3B, 3C, and 3E). Similar results were obtained by FACS analysis.

Figure 4:
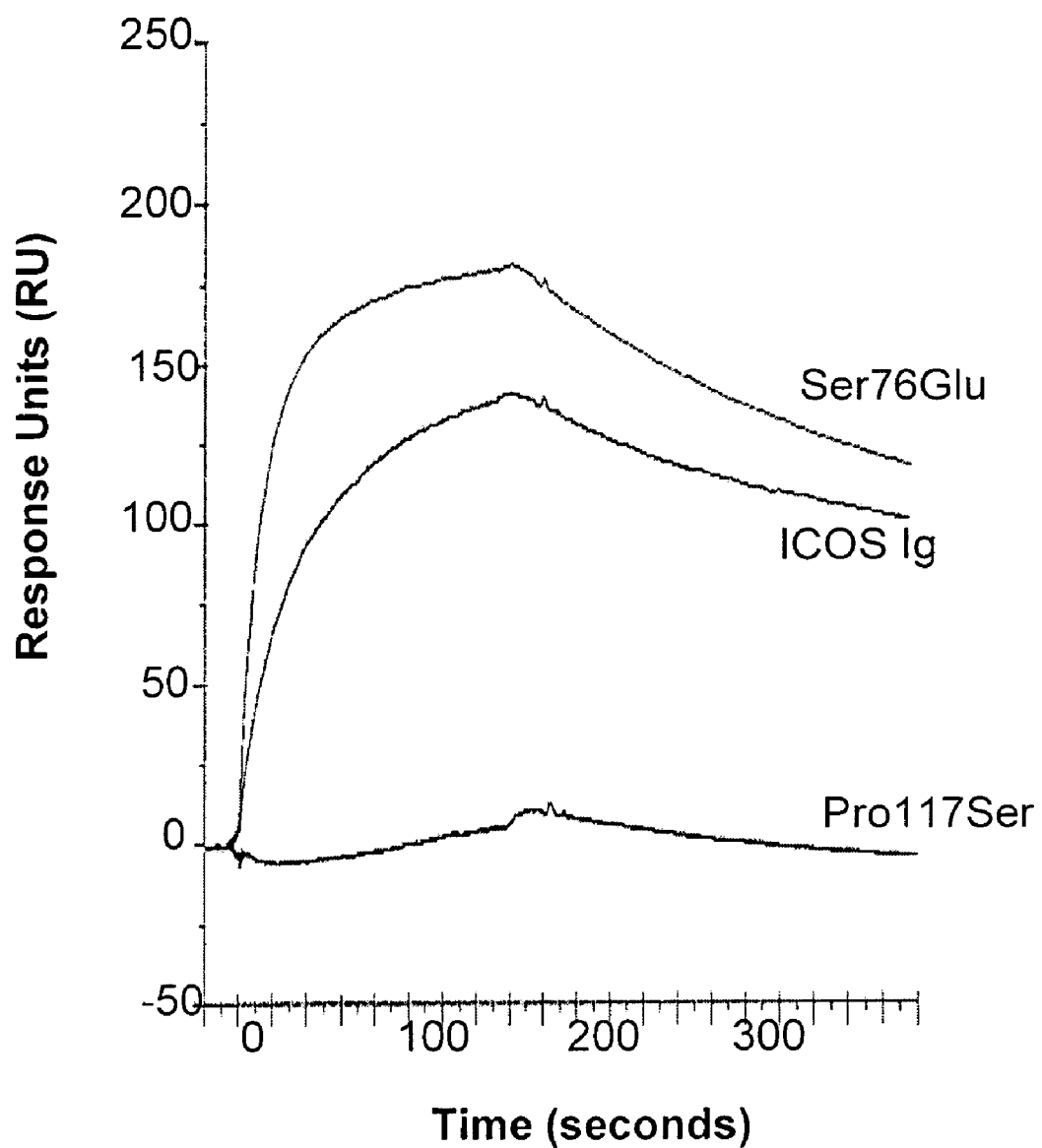
FIG. 4 is a line graph showing the binding of wild-type and mutant ICOSIg to B7-H2, as determined by surface plasmon resonance analysis.

Binding analysis by BIAcore: The binding of wild-type and mutant ICOSIg to B7-H2 was analyzed by surface plasmon resonance. B7-H2Ig was immobilized on a sensor chip and equal concentrations of wild-type and mutant ICOSIg polypeptides in fluid phase were passed over the chip. The binding response of each polypeptide [measured in arbitrary response units (RU)] was calculated by subtracting the response seen with an uncoated control surface from the response observed with the B7-H2Ig-coated surface. Similar to the results obtained by ELISA, equilibrium binding curves showed that in the applied concentration, Ser76Glu and wide-type ICOSIg had significant binding responses, while the Pro117Ser mutant showed minimal binding to the sensor chips (FIG. 4). Binding of Ser76Glu reached equilibrium faster than wild type ICOSIg, although their dissociation rates were similar. These results suggest that the Ser76Glu mutant binds to B7-H2 with higher avidity than wild-type ICOS.

Figure 5A:
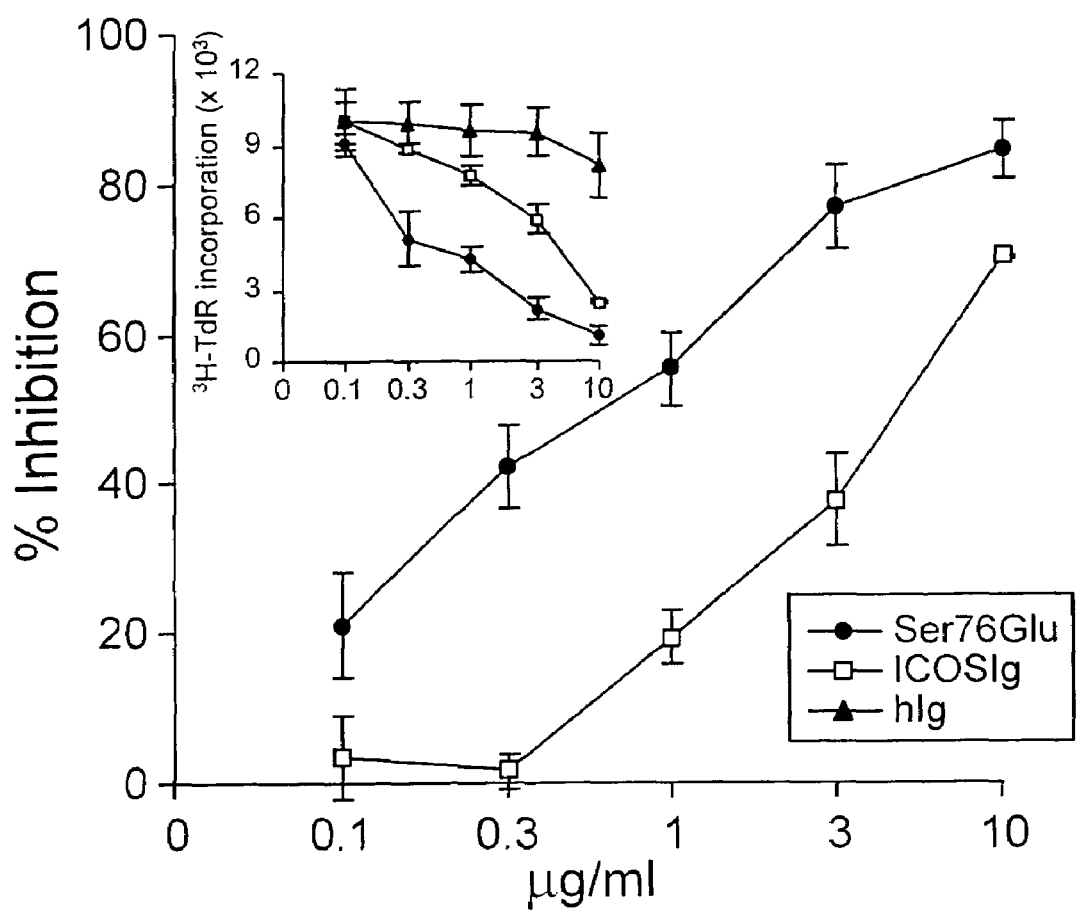
FIGS. 5A and 5B are line graphs depicting the effect of either ICOSIg or the Ser76Glu ICOS mutant on T cell proliferation in the presence of anti-CD3 mAb (FIG. 5A) or irradiated allogeneic adherent cells (FIG. 5B).

Inhibition of T cell responses by ICOS mutant Ser76Glu: Since ICOSIg mutant Ser76Glu demonstrated a higher apparent avidity for B7-H2Ig than the Lys52Ser mutant, Ser76Glu was used in further experiments determine whether the increased avidity was correlated with an increased ability to block the function of B7-H2. Previous studies showed that immobilized B7-H2Ig could costimulate T cell proliferation and cytokine production in the presence of sub optimal doses of anti-CD3 to mimic the TCR signal (Wang et al., supra). The same system was used to test the effect of Ser76Glu. As shown in FIG. 5A, wild-type ICOSIg at 1–10 µg/ml significantly blocked the costimulatory effect of immobilized B7-H2Ig on purified human T cells. Addition of the Ser76Glu protein to the culture resulted in a stronger inhibition of the costimulatory effect. Ser76Glu was approximately 10-fold more effective than wild-type ICOSIg at these concentrations; furthermore, the effect of Ser76Glu was observed even at 0.1 µg/ml, while wild-type ICOSIg at the same concentration did not inhibit T cell proliferation.

TABLE 3

ICOS mutants and their relative specific binding activities

| Mutant | Substitution [a] | | B7-H2 Binding[d] |
|---|---|---|---|
| | Nucleic Acid[b] | Amino Acid[c] | |
| ICOSIg | — | — | 100 |
| RP49–52 | ICOS$^{145-156}$/CD28$^{145-156}$ | ICOS$^{49-52}$/CD28$^{49-52}$ | 9 |
| RP64–78 | ICOS$^{190-234}$/CD28$^{199-243}$ | ICOS$^{64-78}$/CD28$^{67-81}$ | <0.1 |
| RP114–119 | ICOS$^{340-357}$/CD28$^{349-366}$ | ICSO$^{114-119}$/CD28$^{117-122}$ | <0.1 |
| Gln49Ser | CAG/TCG | Gln$^{49}$Ser | 33 |
| Gln50Ser | CAA/TCA | Gln$^{50}$Ser | 6 |
| Phe51Ser | TTT/TCT | Phe$^{51}$Ser | <0.1 |
| Lys52Ser | AAA/AGC | Lys$^{52}$Ser | 200 |
| Asp64Ser | GAT/TCT | Asp$^{64}$Ser | 6 |
| Lys67Ser | AAG/AGC | Lys$^{67}$Ser | <0.1 |
| Lys69Ser | AAA/AGC | Lys$^{69}$Ser | 3 |
| Ser76Glu | TCC/GAA | Ser$^{76}$Glu | 300 |
| Phe114Ser | TTT/TCT | Phe$^{114}$Ser | <0.1 |
| Asp115Ser | GAT/TCT | Asp$^{115}$Ser | <0.1 |
| Pro117Ser | CCT/TCT | Pro$^{117}$Ser | <0.1 |
| Phe119Ser | TTT/TCT | Phe$^{119}$Ser | <0.1 |

[a]The regions, nucleotides, or amino acids in front of the slash were replaced with the corresponding regions, nucleotides, or amino acids after the slash.
[b]Nucleotides are numbered from the A of the initiation codon.
[c]Amino acids are numbered from the initiation methionine.
[d]Specific binding activities were determined for each of the indicated fusion proteins. The concentration of a fusion protein required to give an arbitrary A405, which is the same as that of wild type ICOSIg, was determined from the linear region of binding curves and expressed as a percentage of specific binding activity of ICOSIg. Values represent the average of three determinations from each binding curve. The results are representative of three experiments.

Figure 5B:
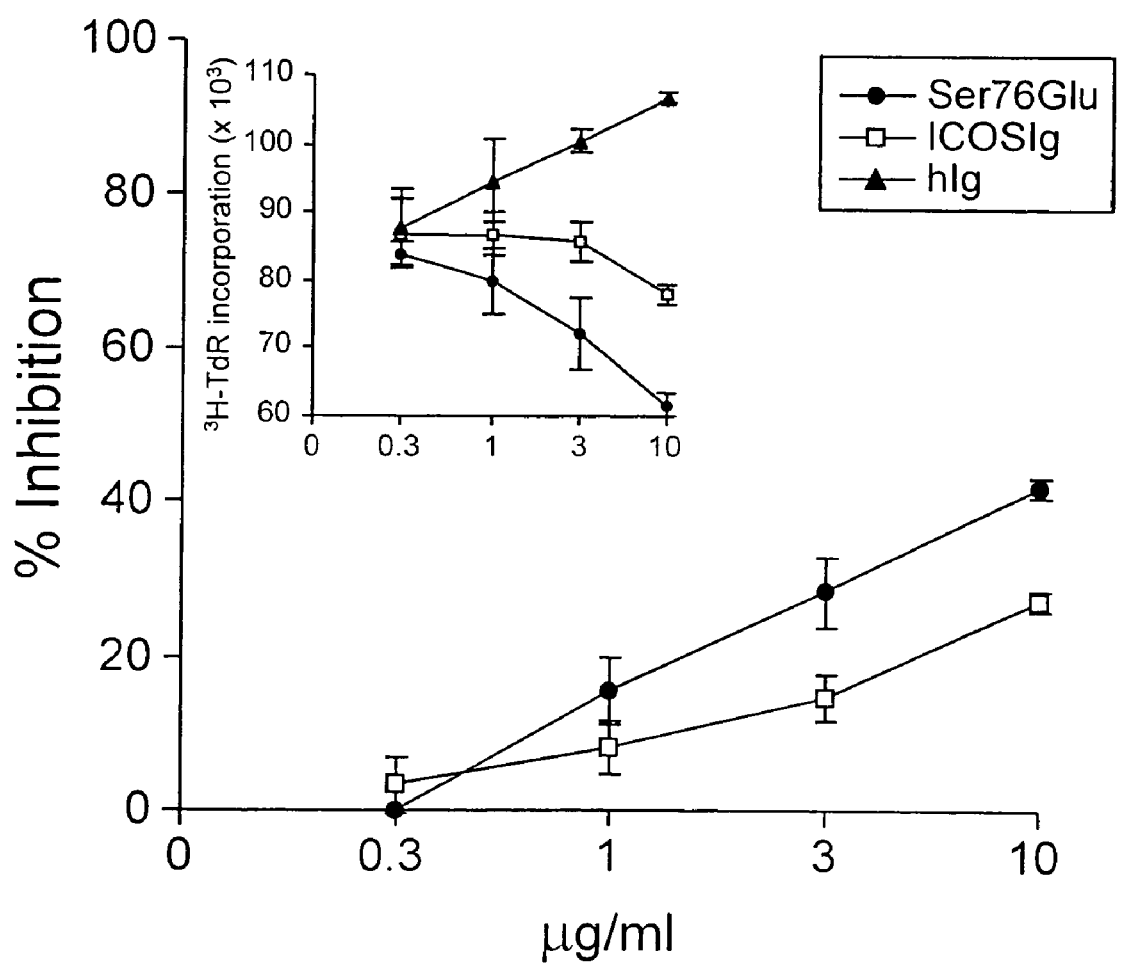

To explore the effect of Ser76Glu under more physiological conditions, the mutant also was tested in one-way mixed lymphocyte reactions (MLR) to allogeneic antigens. Wild-type ICOSIg inhibited T cell proliferation in MLR by up to 25% at 10 μg/ml, as compared to the control Ig. Ser76Glu blocked T cell proliferation by up to 43% ($p<0.01$) at the same concentration (FIG. 5B). Ser76Glu therefore is superior to wild-type ICOSIg in the inhibition of T cell responses to allogeneic antigens.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified polypeptide consisting of:

(a) a variant of a wild-type ICOS amino acid sequence consisting of an extracellular domain of wild-type ICOS, the wild-type ICOS extracellular domain being SEQ ID NO:10 or SEQ ID NO:9, the variant:

consisting of an amino acid sequence that differs by one or more amino acid substitutions from, but is at least 85% homologous to, its corresponding wild-type ICOS amino acid sequence; and having altered affinity for human B7-H2 (SEQ ID NO:43) compared to its corresponding wild-type ICOS amino acid sequence, wherein said affinity for human B7-H2 is increased by at least 10% relative to the affinity of the corresponding wild-type ICOS amino acid sequence for human B7-H2; or (b) the variant of (a) and: (I) a peptide sequence unrelated to ICOS attached to the N-terminus of the variant of (a); (II) a peptide sequence unrelated to ICOS attached to the C-terminus of the variant of (a); or (III) a peptide sequence unrelated to ICOS attached to the N-terminus of the variant of (a) and a second peptide sequence unrelated to ICOS attached to the C-terminus of the variant of (a).

2. The purified polypeptide of claim 1, wherein the variant differs from its corresponding wild-type amino acid sequence at a position corresponding to amino acid 76 of SEQ ID NO:12.

3. The purified polypeptide of claim 2, wherein, in the variant, the amino acid at the position corresponding to said amino acid 76 of SEQ ID NO:12 is glutamine.

4. The purified polypeptide of claim 1, wherein the variant differs from its corresponding wild-type amino acid sequence at a position corresponding to amino acid 52 of SEQ ID NO:12.

5. The purified polypeptide of claim 4, wherein, in the variant, the amino acid at the position corresponding to said amino acid 52 of SEQ ID NO:12 is serine.

6. The purified polypeptide of claim 1, wherein said variant is capable of inhibiting T cell activation in a T cell proliferation assay.

7. The purified polypeptide of claim 1, wherein the peptide sequence unrelated to the ICOS or the second peptide sequence unrelated to ICOS is a blocking agent that facilitates survival of the polypeptide in vivo.

8. The purified polypeptide of claim 1, wherein the peptide sequence unrelated to the ICOS or the second peptide sequence unrelated to ICOS is a tag amino acid sequence.

9. The purified polypeptide of claim 1, wherein the peptide sequence unrelated to the ICOS or the second peptide sequence unrelated to ICOS is a human IgG1 CH2-CH3 sequence.

* * * * *

SEQUENCE LISTING

<160> NUMBER OF SEQ ID NOS: 42

<210> SEQ ID NO 1
<211> LENGTH: 96
<212> TYPE: PRT
<213> ORGANISM: Mus musculus

<400> SEQUENCE: 1

```
Val Thr Gln Pro Ser Val Leu Ala Ser Ser His Gly Val Ala Ser Phe
1               5                   10                  15

Pro Cys Glu Ser Pro Ser His Asn Thr Asp Val Val Thr Val Leu Gln
            20                  25                  30

Thr Asn Asp Gln Met Thr Val Ala Thr Thr Phe Thr Glu Lys Asn Thr
        35                  40                  45

Val Gly Phe Leu Asp Tyr Pro Phe Ser Gly Thr Phe Asn Glu Ser Arg
    50                  55                  60

Val Asn Leu Thr Ile Gln Gly Leu Arg Ala Val Asp Gly Leu Tyr Leu
65                  70                  75                  80

Cys Val Leu Phe Val Gly Met Gly Gln Ile Tyr Val Ile Pro Glu Pro
                85                  90                  95
```

<210> SEQ ID NO 2
<211> LENGTH: 96
<212> TYPE: PRT
<213> ORGANISM: Rattus norvegicus

<400> SEQUENCE: 2

```
Val Thr Gln Pro Ser Val Leu Ala Ser Ser His Gly Val Ala Ser Phe
1               5                   10                  15

Pro Cys Glu Ala Ser Ser His Asn Thr Asp Val Val Thr Val Leu Gln
            20                  25                  30

Thr Asn Asp Gln Val Thr Val Ala Thr Thr Phe Thr Val Lys Asn Thr
        35                  40                  45

Leu Gly Phe Leu Asp Asp Pro Phe Ser Gly Thr Phe Asn Glu Ser Arg
    50                  55                  60

Val Asn Leu Thr Ile Gln Gly Leu Arg Ala Ala Asp Gly Leu Tyr Phe
65                  70                  75                  80

Cys Val Leu Phe Val Gly Met Gly Gln Ile Tyr Val Ile Pro Glu Pro
                85                  90                  95
```

<210> SEQ ID NO 3
<211> LENGTH: 96
<212> TYPE: PRT
<213> ORGANISM: Homo sapiens

<400> SEQUENCE: 3

```
Val Ala Gln Pro Ala Val Leu Ala Ser Ser Arg Gly Ile Ala Ser Phe
1               5                   10                  15
```

```
Val Cys Glu Ala Ser Pro Gly Lys Ala Thr Val Thr Val Leu Gln
            20                  25                  30

Ala Asp Ser Gln Val Thr Val Ala Ala Thr Tyr Met Met Gly Asn Glu
            35                  40                  45

Leu Thr Phe Leu Asp Asp Ser Ile Thr Gly Thr Ser Ser Gly Asn Gln
    50                  55                  60

Val Asn Leu Thr Ile Gln Gly Leu Arg Ala Met Asp Gly Leu Tyr Ile
65                  70                  75                  80

Cys Val Leu Tyr Leu Gly Ile Gly Gln Ile Tyr Val Ile Pro Glu Pro
                85                  90                  95

<210> SEQ ID NO 4
<211> LENGTH: 96
<212> TYPE: PRT
<213> ORGANISM: Bos taurus

<400> SEQUENCE: 4

Val Ser Gln Pro Ala Val Leu Ala Ser Ser Arg Gly Val Ala Ser Phe
1               5                   10                  15

Val Cys Glu Ala Ser Ser His Lys Ala Thr Val Thr Val Leu Gln
            20                  25                  30

Ala Asn Ser Gln Met Thr Val Ala Met Thr Tyr Thr Val Glu Asn Glu
            35                  40                  45

Leu Thr Phe Ile Asp Asp Ser Thr Gly Ile Ser His Gly Asn Lys
    50                  55                  60

Val Asn Leu Thr Ile Gln Gly Leu Ser Ala Met Asp Gly Leu Tyr Ile
65                  70                  75                  80

Cys Val Leu Tyr Val Gly Met Gly Gln Ile Tyr Val Ile Pro Glu Pro
                85                  90                  95

<210> SEQ ID NO 5
<211> LENGTH: 95
<212> TYPE: PRT
<213> ORGANISM: Mus musculus

<400> SEQUENCE: 5

Val Gln Pro Leu Val Asp Ser Glu Ser Leu Cys Leu Ala Ala Leu Tyr
1               5                   10                  15

Gly Val Asn Asp Val Gly Asn Gly Asn Phe Thr Tyr Gln Pro Gln Phe
            20                  25                  30

Arg Ser Asn Ala Glu Phe Asn Cys Asp Gly Asp Phe Asp Asn Glu Thr
            35                  40                  45

Val Thr Phe Arg Leu Trp Asn Leu His Val Asn His Thr Asp Ile Tyr
    50                  55                  60

Phe Cys Lys Ile Glu Phe Met Tyr Pro Pro Tyr Leu Asp Asn Glu
65                  70                  75                  80

Arg Ser Asn Gly Thr Ile Ile His Ile Lys Glu Lys His Leu Cys
                85                  90                  95

<210> SEQ ID NO 6
<211> LENGTH: 95
<212> TYPE: PRT
<213> ORGANISM: Rattus norvegicus

<400> SEQUENCE: 6

Val Gln Pro Leu Val Asp Asn Glu Ser Leu Cys Leu Ala Ala Leu Tyr
1               5                   10                  15

Gly Val Asn Asp Val Gly Asn Gly Asn Phe Thr Tyr Gln Pro Gln Phe
```

```
                20              25              30
Arg Pro Asn Val Gly Phe Asn Cys Asp Gly Asn Phe Asp Asn Glu Thr
             35                  40                  45

Val Thr Phe Arg Leu Trp Asn Leu Asp Val Asn His Thr Asp Ile Tyr
 50                      55                  60

Phe Cys Lys Ile Glu Val Met Tyr Pro Pro Tyr Leu Asp Asn Glu
 65                  70                  75                  80

Lys Ser Asn Gly Thr Ile Ile His Ile Lys Glu Lys His Leu Cys
                 85                  90                  95

<210> SEQ ID NO 7
<211> LENGTH: 95
<212> TYPE: PRT
<213> ORGANISM: Bos taurus

<400> SEQUENCE: 7

Val Gln Pro Met Val Asn Asn Glu Asn Leu Cys Phe Ser Ala Leu Tyr
 1               5                  10                  15

Gly Ala Asp Ala Val Asn Gly Asn Phe Ser His Pro His Gln Phe
             20                  25                  30

His Ser Thr Thr Gly Phe Asn Cys Asp Gly Lys Leu Gly Asn Glu Thr
             35                  40                  45

Val Thr Phe Tyr Leu Lys Asn Leu Tyr Val Asn Gln Thr Asp Ile Tyr
 50                      55                  60

Phe Cys Lys Ile Glu Val Met Tyr Pro Pro Tyr Leu Asp Asn Glu
 65                  70                  75                  80

Lys Ser Asn Gly Thr Ile Ile His Val Lys Glu Gln His Phe Cys
                 85                  90                  95

<210> SEQ ID NO 8
<211> LENGTH: 95
<212> TYPE: PRT
<213> ORGANISM: Homo sapiens

<400> SEQUENCE: 8

Val Gln Pro Met Ala Tyr Asp Ala Asn Leu Cys Phe Ser Ala Leu His
 1               5                  10                  15

Gly Leu Asp Ala Val Val Tyr Gly Asn Tyr Ser Gln Gln Leu Gln Val
             20                  25                  30

Tyr Ser Lys Thr Gly Phe Asn Cys Asp Gly Lys Leu Gly Asn Glu Ser
             35                  40                  45

Val Thr Phe Tyr Leu Gln Asn Leu Tyr Val Asn Gln Thr Asp Ile Tyr
 50                      55                  60

Phe Cys Lys Ile Glu Val Met Tyr Pro Pro Tyr Leu Asp Asn Glu
 65                  70                  75                  80

Lys Ser Asn Gly Thr Ile Ile His Val Lys Glu Lys His Leu Cys
                 85                  90                  95

<210> SEQ ID NO 9
<211> LENGTH: 112
<212> TYPE: PRT
<213> ORGANISM: Mus musculus

<400> SEQUENCE: 9

Ala Asp His Arg Met Phe Ser Phe His Asn Gly Gly Val Gln Ile Ser
 1               5                  10                  15

Cys Lys Tyr Pro Asp Ile Val Gln Gln Leu Lys Met Arg Leu Phe Arg
             20                  25                  30
```

```
Glu Arg Glu Val Leu Cys Glu Leu Thr Lys Thr Lys Gly Ser Gly Asn
            35                  40                  45

Ala Val Ser Ile Lys Asn Pro Met Leu Cys Leu Tyr His Leu Ser Asn
 50                  55                  60

Asn Ser Val Ser Phe Phe Leu Asn Asn Pro Asp Ser Gln Gly Ser
65                  70                  75                  80

Tyr Tyr Phe Cys Ser Leu Ser Ile Phe Asp Pro Pro Phe Gln Glu
                85                  90                  95

Arg Asn Leu Ser Gly Gly Tyr Leu His Ile Tyr Glu Ser Gln Leu Cys
               100                 105                 110

<210> SEQ ID NO 10
<211> LENGTH: 111
<212> TYPE: PRT
<213> ORGANISM: Homo sapiens

<400> SEQUENCE: 10

Ala Asn Tyr Glu Met Phe Ile Phe His Asn Gly Gly Val Gln Ile Leu
 1               5                  10                  15

Cys Lys Tyr Pro Asp Ile Val Gln Gln Phe Lys Met Gln Leu Leu Lys
                20                  25                  30

Gly Gly Gln Ile Leu Cys Asp Leu Thr Lys Thr Lys Gly Ser Gly Asn
            35                  40                  45

Thr Val Ser Ile Lys Ser Leu Lys Phe Cys His Ser Gln Leu Ser Asn
 50                  55                  60

Asn Ser Val Ser Phe Phe Leu Tyr Asn Leu Asp His Ser His Ala Asn
65                  70                  75                  80

Tyr Tyr Phe Cys Asn Leu Ser Ile Phe Asp Pro Pro Phe Lys Val
                85                  90                  95

Thr Leu Thr Gly Gly Tyr Leu His Ile Tyr Glu Ser Gln Leu Cys
               100                 105                 110

<210> SEQ ID NO 11
<211> LENGTH: 6
<212> TYPE: PRT
<213> ORGANISM: Homo sapiens

<400> SEQUENCE: 11

Met Tyr Pro Pro Pro Tyr
 1               5

<210> SEQ ID NO 12
<211> LENGTH: 199
<212> TYPE: PRT
<213> ORGANISM: Homo sapiens

<400> SEQUENCE: 12

Met Lys Ser Gly Leu Trp Tyr Phe Phe Leu Phe Cys Leu Arg Ile Lys
 1               5                  10                  15

Val Leu Thr Gly Glu Ile Asn Gly Ser Ala Asn Tyr Glu Met Phe Ile
                20                  25                  30

Phe His Asn Gly Gly Val Gln Ile Leu Cys Lys Tyr Pro Asp Ile Val
            35                  40                  45

Gln Gln Phe Lys Met Gln Leu Leu Lys Gly Gly Gln Ile Leu Cys Asp
 50                  55                  60

Leu Thr Lys Thr Lys Gly Ser Gly Asn Thr Val Ser Ile Lys Ser Leu
65                  70                  75                  80
```

```
            Lys Phe Cys His Ser Gln Leu Ser Asn Asn Ser Val Ser Phe Phe Leu
                            85                  90                  95

Tyr Asn Leu Asp His Ser His Ala Asn Tyr Tyr Phe Cys Asn Leu Ser
                        100                 105                 110

Ile Phe Asp Pro Pro Phe Lys Val Thr Leu Thr Gly Gly Tyr Leu
                    115                 120                 125

His Ile Tyr Glu Ser Gln Leu Cys Cys Gln Leu Lys Phe Trp Leu Pro
            130                 135                 140

Ile Gly Cys Ala Ala Phe Val Val Cys Ile Leu Gly Cys Ile Leu
            145                 150                 155                 160

Ile Cys Trp Leu Thr Lys Lys Tyr Ser Ser Val His Asp Pro
                            165                 170                 175

Asn Gly Glu Tyr Met Phe Met Arg Ala Val Asn Thr Ala Lys Lys Ser
                        180                 185                 190

Arg Leu Thr Asp Val Thr Leu
                    195
```

<210> SEQ ID NO 13
<211> LENGTH: 62
<212> TYPE: DNA
<213> ORGANISM: Artificial Sequence
<220> FEATURE:
<223> OTHER INFORMATION: Primer

<400> SEQUENCE: 13
ttatgcaaat atcctgacat tgtcagggag ttccggatgc agttgctgaa agggggcaa     60 at                                                                  62

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
gacaatgtca ggatatttgc at                                            22

<210> SEQ ID NO 15
<211> LENGTH: 59
<212> TYPE: DNA
<213> ORGANISM: Artificial Sequence
<220> FEATURE:
<223> OTHER INFORMATION: Primer

<400> SEQUENCE: 15
ttactcccag cagcttcagg tttactcaaa aagtctgaaa ttctgccatt ctcagttat    59

<210> SEQ ID NO 16
<211> LENGTH: 66
<212> TYPE: DNA
<213> ORGANISM: Artificial Sequence
<220> FEATURE:
<223> OTHER INFORMATION: Primer

<400> SEQUENCE: 16
taaacctgaa gctgctggga gtaattccca tatacaacgc agagtatttg ccccccttc     60 agcaac                                                              66

<210> SEQ ID NO 17
<211> LENGTH: 42

```
<212> TYPE: DNA
<213> ORGANISM: Artificial Sequence
<220> FEATURE:
<223> OTHER INFORMATION: Primer

<400> SEQUENCE: 17
tattacttct gcaacctatc aattgctgct cctcctcctt tt                    42

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
agcaattgat aggttgcaga agt                                         23

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
cctgacattg tctcgcaatt taaaatgcag                                  30

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
ctgcatttta aattgcgaga caatgtcagg                                  30

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
cctgacattg tccagtcatt taaaatgcag                                  30

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
ctgcatttta aatgactgga caatgtcagg                                  30

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
```
gtccagcaat ctaaaatgca g                                             21

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
ctgcatttta gattgctgga c                                             21

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
gtccagcaat ttagcatgca gttgctg                                       27

<210> SEQ ID NO 26
<211> LENGTH: 26
<212> TYPE: DNA
<213> ORGANISM: Artificial Sequence
<220> FEATURE:
<223> OTHER INFORMATION: Primer

<400> SEQUENCE: 26
cagcaactgc atgctaaatt gctgga                                        26

<210> SEQ ID NO 27
<211> LENGTH: 34
<212> TYPE: DNA
<213> ORGANISM: Artificial Sequence
<220> FEATURE:
<223> OTHER INFORMATION: Primer

<400> SEQUENCE: 27
ggcaaatact ctgctctctc actaagacaa aagg                               34

<210> SEQ ID NO 28
<211> LENGTH: 34
<212> TYPE: DNA
<213> ORGANISM: Artificial Sequence
<220> FEATURE:
<223> OTHER INFORMATION: Primer

<400> SEQUENCE: 28
ccttttgtct tagtgagaga gcagagtatt tgcc                               34

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
ctgcgatctc actagcacaa aaggaagtgg                                    30

<210> SEQ ID NO 30
<211> LENGTH: 30
<212> TYPE: DNA
<213> ORGANISM: Artificial Sequence

```
<220> FEATURE:
<223> OTHER INFORMATION: Primer

<400> SEQUENCE: 30
ccacttcctt ttgtgctagt gagatcgcag                                          30

<210> SEQ ID NO 31
<211> LENGTH: 28
<212> TYPE: DNA
<213> ORGANISM: Artificial Sequence
<220> FEATURE:
<223> OTHER INFORMATION: Primer

<400> SEQUENCE: 31
gcgatctcac taagacaagc ggaagtgg                                            28

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
ccacttccgc ttgtcttagt gagatcgc                                            28

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
gtggaaacac agtggaaatt aagagtctg                                           29

<210> SEQ ID NO 34
<211> LENGTH: 29
<212> TYPE: DNA
<213> ORGANISM: Artificial Sequence
<220> FEATURE:
<223> OTHER INFORMATION: Primer

<400> SEQUENCE: 34
cagactctta atttccactg tgtttccac                                           29

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
cctatcaatt tctgatcctc ctcc                                                24

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
ggaggaggat cagaaattga tagg                                                24
```

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
cctatcaatt ttttctcctc ctcc                                              24

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ggaggaggag aaaaaattga tagg                                              24

<210> SEQ ID NO 39
<211> LENGTH: 27
<212> TYPE: DNA
<213> ORGANISM: Artificial Sequence
<220> FEATURE:
<223> OTHER INFORMATION: Primer

<400> SEQUENCE: 39
caatttttga tccttctcct tttaaag                                           27

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
ctttaaaagg agaaggatca aaaattg                                           27

<210> SEQ ID NO 41
<211> LENGTH: 28
<212> TYPE: DNA
<213> ORGANISM: Artificial Sequence
<220> FEATURE:
<223> OTHER INFORMATION: Primer

<400> SEQUENCE: 41
cctcctcctt ctaaagtaac tcttacag                                          28

<210> SEQ ID NO 42
<211> LENGTH: 28
<212> TYPE: DNA
<213> ORGANISM: Artificial Sequence
<220> FEATURE:
<223> OTHER INFORMATION: Primer

<400> SEQUENCE: 42
ctgtaagagt tactttagaa ggaggagg                                          28